(12) United States Patent
Manita

(10) Patent No.: US 6,582,970 B1
(45) Date of Patent: Jun. 24, 2003

(54) SIMPLE IMMUNOCHEMICAL SEMI-QUANTITATIVE ASSAY METHOD AND APPARATUS

(75) Inventor: Hideaki Manita, Sagamihara (JP)

(73) Assignee: Teikoku Hormone MFG. Co, Ltd., Tokyo (JP)

( * ) Notice: Subject to any disclaimer, the term of this patent is extended or adjusted under 35 U.S.C. 154(b) by 0 days.

(21) Appl. No.: 09/602,150

(22) Filed: Jun. 22, 2000

Related U.S. Application Data

(63) Continuation of application No. 08/549,716, filed as application No. PCT/JP94/00875 on May 31, 1994, now Pat. No. 6,177,281.

(30) Foreign Application Priority Data

Jun. 2, 1993 (JP) ............................................. 5-131590

(51) Int. Cl.[7] ............................................. G01N 33/543
(52) U.S. Cl. ........................ 436/518; 436/523; 436/525; 436/533; 436/541; 436/810; 436/818; 436/829; 435/7.1; 435/7.92; 435/7.93; 435/287.2; 422/56; 422/57; 422/58; 422/60; 422/61
(58) Field of Search ................................ 436/518, 525, 436/523, 533, 541, 810, 818, 829; 435/7.1, 7.92, 7.93, 287.2; 422/56, 57, 58, 60, 61

(56) References Cited

U.S. PATENT DOCUMENTS

| | | | |
|---|---|---|---|
| 4,595,661 A | | 6/1986 | Cragle et al. |
| 4,659,678 A | | 4/1987 | Forrest et al. |
| 4,727,024 A | | 2/1988 | Koocher et al. |
| 4,861,711 A | | 8/1989 | Friesen et al. |
| 4,943,522 A | * | 7/1990 | Eisinger et al. ................ 435/7 |
| 5,120,643 A | | 6/1992 | Ching et al. |
| 5,160,486 A | | 11/1992 | Schlipfenbacher et al. |
| 5,391,272 A | | 2/1995 | O'Daley et al. |
| 5,401,667 A | * | 3/1995 | Koike ........................ 436/514 |
| 5,451,504 A | * | 9/1995 | Fitzpatrick et al. ......... 435/7.32 |
| 5,468,606 A | | 11/1995 | Bogart |
| 5,541,069 A | * | 7/1996 | Mortensen et al. ........... 435/7.9 |
| 5,552,276 A | * | 9/1996 | Mochida et al. ................ 435/6 |
| 5,573,921 A | | 11/1996 | Behnke et al. |
| 5,580,794 A | | 12/1996 | Allen |
| 5,648,274 A | | 7/1997 | Chandler |
| 5,674,700 A | | 10/1997 | Maurel |
| 5,726,064 A | | 3/1998 | Robinson et al. |
| 5,753,519 A | | 5/1998 | Durst et al. |
| 5,756,362 A | | 5/1998 | Durst et al. |
| 5,770,460 A | * | 6/1998 | Pawlak et al. ............... 436/510 |
| 5,780,308 A | * | 7/1998 | Ching et al. ................. 436/514 |
| 5,968,839 A | * | 10/1999 | Blatt et al. ................... 436/513 |
| 5,981,203 A | * | 11/1999 | Meyerhoff et al. .......... 435/7.92 |
| 6,177,281 B1 | * | 1/2001 | Manita ........................ 436/518 |
| 6,218,134 B1 | * | 4/2001 | Yamauchi et al. ............ 435/7.9 |

FOREIGN PATENT DOCUMENTS

| | | | |
|---|---|---|---|
| EP | 0516095 | 12/1929 | |
| EP | 0291994 | 11/1988 | |
| EP | 0516095 | 12/1992 | |
| EP | 516095 | * 12/1992 | .......... G01N/33/53 |
| JP | 61-14549 | 12/1985 | |
| JP | 1-503174 | 4/1988 | |
| JP | 64-32169 | 12/1988 | |
| JP | 2-221860 | 12/1989 | |
| JP | 4-351962 | 5/1991 | |
| WO | 93/03175 | 2/1993 | |

* cited by examiner

Primary Examiner—Lynette R. F. Smith
Assistant Examiner—Ginny Allen Portner
(74) Attorney, Agent, or Firm—Nixon & Vanderhye P.C.

(57) ABSTRACT

The present invention relates to a simple immunochemical semi-quantitative assay method according to chromatography, which comprises trapping a certain amount of an analyte in a sample with a predetermined amount of a fixed antibody for the analyte before qualitative analysis of the analyte, the certain amount corresponding to the amount of the fixed antibody, and thereby decreasing a concentration of the analyte to be subjected to subsequent immunochemical qualitative determination, and an apparatus therefor.

5 Claims, 12 Drawing Sheets

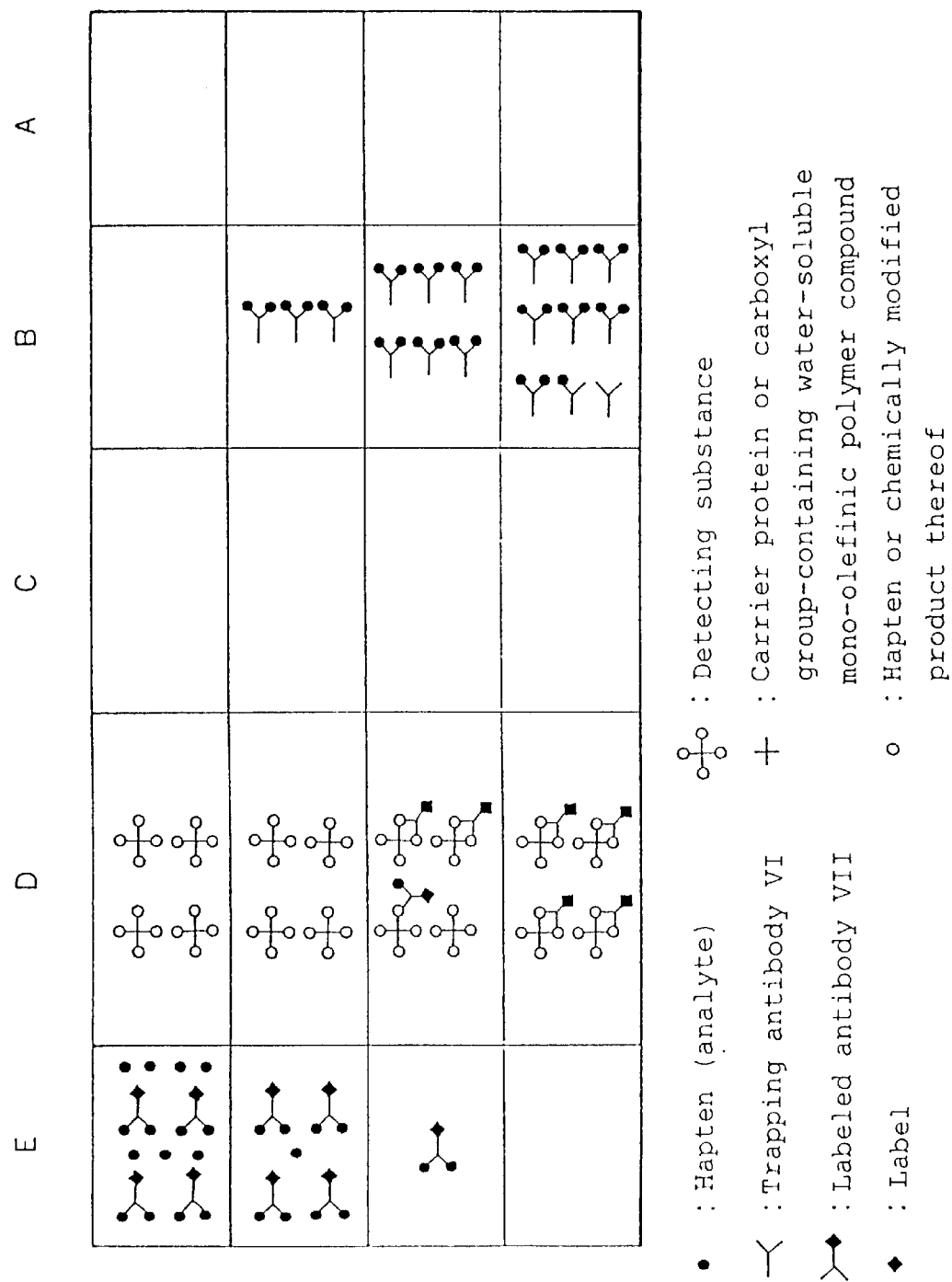

An adhesive double-coated tepe was attached to each top of projections a), b), c) and e).

SIMPLE IMMUNOCHEMICAL SEMI-QUANTITATIVE ASSAY METHOD AND APPARATUS

This application is a continuation of Ser. No. 08/549,716 filed Jun. 11, 1996, now U.S. Pat. No. 6,177,281, which is a 35 U.S.C. §371 of PCT/JP94/00875 filed May 31, 1994.

TECHNICAL FIELD

The present invention relates to an immunochemical method which permits simple semi-quantitative assay without diluting a sample containing an analyte, and an apparatus therefor.

TECHNICAL BACKGROUND

As a method for the qualitative or quantitative determination of a trace amount of a substance contained in an in vivo sample such as blood or urine, immunochemical assay methods are generally used due to their high sensitivity. Of these methods, a so-called immunochromatographic method using chromatography is widely used in many fields, e.g., for clinical examination in a hospital and an assay test in a laboratory.

As a method of detecting an analyte by an immunochromatographic method, a variously labeled specific binding substance (antibody) is reacted with an analyte to be detected (antigen) on a chromatographic material to form a complex of the analyte and the labeled specific binding substance (antigen-antibody complex), and this complex is found (detected) by a variety of means. The label includes radioisotope, chromophore, fluorophore, enzyme, etc. The detecting means include a radiation detector, a spectrophoto meter etc. and visual detection.

JP-A-64-32169 discloses a qualitative assay method by immunochromatography using a colloidal-particles-labeled specific binding substance (antibody) which is chromatographically mobile and capable of generating visually detectable signal, and an apparatus therefor. This publication discloses one means which allows visual detection.

The method described in the above publication is a method for assaying the presence or absence of an analyte (antigen) in a sample or its amount, and comprises (a) bringing a sample containing an analyte (antigen) into contact with a chromatographic medium, (b) moving the above colloidal-particles-labeled substance (labeled antibody) on the chromatographic medium, to allow at least part of the colloidal-particle-labeled substance (labeled antibody) to move to a reactive site and cause a binding reaction, and (c) determining detectable response caused by the colloidal substance in the reaction site for denoting the presence or absence of the analyte (antigen) in the sample and its amount.

Japanese PCT Laid-open Publication No. 1-503174 discloses an apparatus provided with a labeled first antibody which is to specifically bind to an analyte to be detected (antigen) (to be referred to as "labeled first antibody" hereinafter), and is freely mobile on a chromatographic medium in a wet state, and an unlabeled second antibody which is to specifically bind to the analyte (antigen) (the second antibody having an antigen binding portion different from that of the first antibody) (to be referred to as "unlabeled second antibody" hereinafter), and fixed on the chromatographic medium, the apparatus being capable of detecting the presence of the analyte, in a detection area on the chromatographic medium by adding a liquid sample containing the analyte to one end of the chromatographic medium so that the liquid sample moves through the chromatographic medium, reacts with the labeled first antibody and then reacts with the unlabeled second antibody. The principle used in the above apparatus is a so-called (immunochemical) sandwich method.

For determining the amount of an analyte in a sample, conventionally, there is employed a method in which a sample containing an analyte is properly diluted and subjected to a qualitative reaction with a measuring reagent having a predetermined sensitivity and a maximum dilution ratio at which positivity is shown is multiplied by the sensitivity to determine a semi-quantitative assay value, or qualitative reactions are carried out with reagents having different sensitivity without diluting an analyte and the sensitivity of the reagent at which the analyte shows positivity is taken as a semi-quantitative assay value. The method of quantitative analysis includes a liquid-phase assay carried out in a container such as a microtiter well and a solid-phase assay carried out on a chromatographic medium. In the methods described in the above two publications, samples are diluted for carrying out the quantitative determination.

JP-A-4-351962, laid-open recently, discloses a specific-binding analysis method which permits semi-quantitative assay without diluting a sample and an apparatus therefor. In the method described in this publication, for the qualitative or quantitative determination of an analyte in a sample by a chromatographic method, a specific substance is allowed to be present in a measurement system and the amount of a labeled substance to be measured as an index for the analyte is decreased due to the presence of the specific substance, so that there can be consequently obtained a result similar to the result obtained by diluting a sample containing the analyte (to be referred to as "dilution effect" hereinafter).

In a typical method described in the above publication, an analyte (a) added to a sample addition portion contacts a predetermined amount (concentration) of a specific substance (b), which is present on a chromatographic material without being fixed, and a predetermined amount of a labeled specific-binding substance (e), which is present on the chromatographic material without being fixed, (in a site where the specific-binding substance is present). A certain amount of the analyte (a) bonds to the specific substance (b). When, however, an excess of the analyte (a) over the specific substance (b) is present, the excess of the analyte (a) moves to a portion (detection portion) where a specific-binding substance (specific substance (b) or a substance (g) capable of binding to that portion of the analyte (a) which the specific substance (b) bonds to) is present being fixed to the chromatographic material while the excess of the analyte (a) retains a portion capable of binding to the specific substance (b). The analyte (a) which has no portion capable of binding to the specific substance (b), or at least has bound to the specific substance (b), passes the detection portion. Only a complex (f) of the analyte (a)—the labeled specific-binding substance (e), which at least has a portion capable of binding to the specific substance (b), is fixed on the detection portion, and this fixed complex (f) is detected by various means.

It has been generally required to dilute a sample for semi-quantitative assaying an analyte in the sample. Further, the method using reagents having different sensitivity, which does not require the dilution of a sample, has a defect in that the determination is difficult since the intensity of one reaction in one measurement sensitivity is different from the intensity of another reaction in another measurement sensitivity, so that this method has been scarcely practically used.

In the field of medical treatment, clinical examination in particular, the operation of diluting a sample increases the possibility of an examiner being infected with pathogen from blood, urine, etc., as testing samples. Further, when a large number of samples are semi-quantitative assayed, the operation efficiency can be remarkably improved if the dilution operation is not necessary. It is therefore an object of the present invention to provide a simple immunochemical semi-quantitative assay method which does not require the dilution of a sample, and an apparatus therefor.

Like the present invention, the above-described JP-A-4-351962 discloses an invention which does not require the dilution of a sample. In the method of this publication, many factors are concerned with the adjustment of "dilution effect" of a sample, and it is difficult to adjust the dilution effect, so that no narrow semi-quantitative assay value width can be set and that the method has a problem in measurement accuracy. It is further an object of the present invention to provide an immunochemical semi-quantitative assay method in which the number of factors concerned with the adjustment of "dilution effect" is small so that the dilution effect can be easily adjusted and the sensitivity can be improved, i.e., a semi-quantitative assay value width can be narrowly set, and an apparatus therefor.

DISCLOSURE OF THE INVENTION

For achieving the above objects, the present inventor has made diligent studies, and has found that the above objects are achieved by a simple immunochemical semi-quantitative assay method according to chromatography, which comprises trapping a certain amount of an analyte in a sample with a predetermined amount of a fixed antibody for the analyte before qualitative analysis of the analyte, the certain amount corresponding to the amount of the fixed antibody, and thereby decreasing a concentration of the analyte to be subjected to subsequent immunochemical qualitative determination, and a simple immunochemical semi-quantitative assay apparatus according to immunochromatography, which comprises a sample addition portion (A) for adding a sample containing an analyte, an antibody-fixed portion (B) where an antibody for trapping a certain amount of the analyte in the sample is present being fixed in a predetermined amount, a labeled substance presence portion (C) where a labeled substance as an index for detecting the presence or absence of the analyte in the sample is present in a chromatographically mobile state, a detection portion (D) where a detecting substance for detecting the labeled substance is present being fixed, and an absorption portion (E) for removing the labeled substance which does not participate in the detection of the analyte, together with the added sample, by absorption.

In the semi-quantitative assay method and the apparatus of the present invention, in a series of chromatographic analysis, a certain amount of an analyte in a sample is trapped with a fixed antibody before qualitative determination so that the amount (concentration) of the analyte in the sample to be subjected to qualitative determination is decreased in advance, whereby the same effect (dilution effect) as that produced by qualitative determination by immunochromatography after the dilution of the sample containing the analyte can be obtained.

That is, the assay is carried out by adding the same sample to several units in which the fixed amounts of a trapping antibody are changed stepwise (the sample being to have a different dilution degree in each unit), whereby, in the subsequent qualitative analysis in each unit having common sensitivity, the semi-quantitative assay value of an analyte in the sample can be determined on the basis of the fixed amount of the trapping antibody set at the unit in which the analysis result changes from positivity to negativity or from negativity to positivity.

BRIEF DESCRIPTION OF DRAWINGS

FIG. 9 shows the principle of the semi-quantitative assay method of the present invention when the analyte is a hapten (at the time when the assay has been completed).

PREFERRED EMBODIMENTS FOR WORKING THE INVENTION

Figure 1:
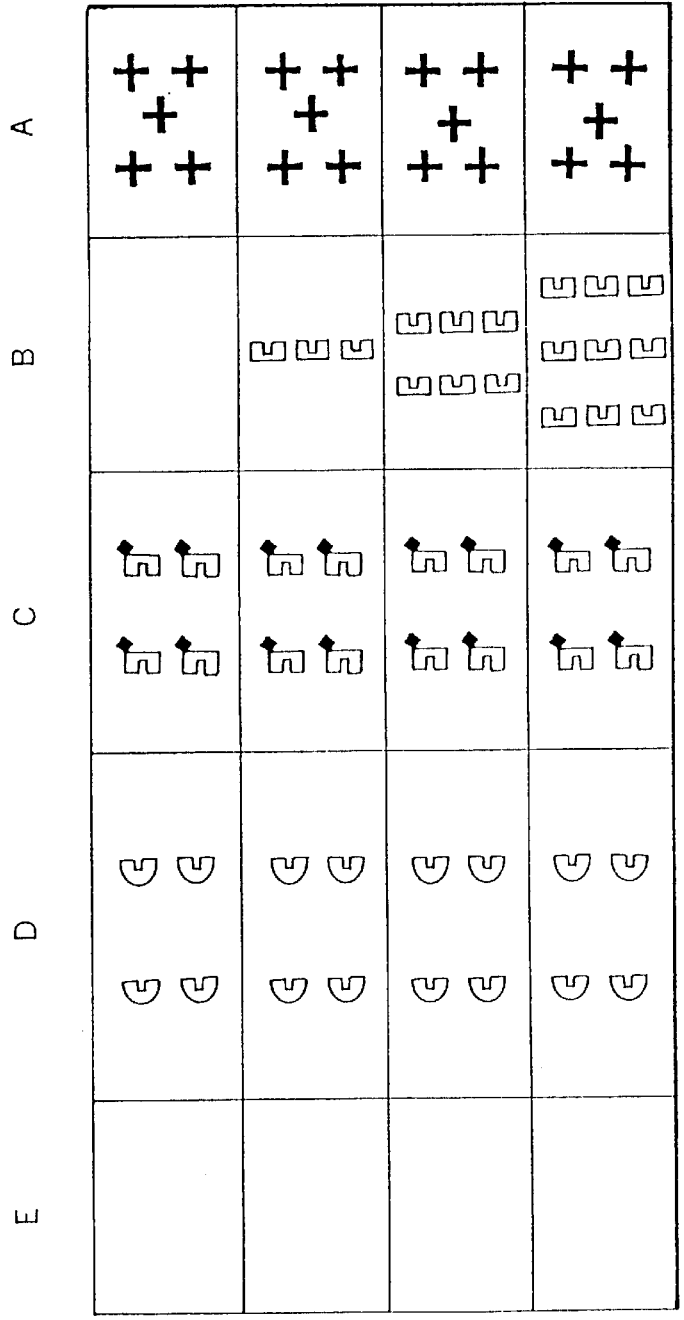
FIG. 1 shows the principle of the semi-quantitative assay method of the present invention when the analyte is a complete antigen (at the time when a sample is added).

The present invention will be explained in detail hereinafter.

The analyte that can be used in the present invention is largely classified into a complete antigen and a hapten (incomplete antigen).

The above complete antigen refers to an antigenic substance which itself has the capability of inducing the antibody production (immunogenicity), and mainly includes peptide hormones having high molecular weights. The above hapten (incomplete antigen) refers to that which can bind to an antibody but has no capability of inducing the antibody production by itself, and includes peptides having relatively small molecular weights (molecular weight of about 1,000 or less). Hapten acquires the antibody production capability when bound to a protein such as bovine serum albumin. Specific examples of these are shown below, while they shall not be limited to those described below.

Examples of Complete Antigen (1) Examples of Peptide Hormone

1) Pituitary hormones such as growth hormone (GH), adrenocorticotropic hormone (ACTH), melanocyte-stimulating hormone (MSH), prolactin, thyroid-stimulating hormone (TSH), luteinizing hormone (LH), follicle-stimulating hormone (FSH) and oxytocin.
2) Calcium metabolic regulation hormones such as calcitonin and parathyroid hormone.
3) Insulin, proinsulin and pancreatic hormone.
4) Alimentary canal hormones such as gastrin and secretin.
5) Hormones which act on blood vessels such as angiotensin and bradykinin.
6) Placental hormones such as human chorionic gonadotropin (hCG) and human placental lactogen (hPL).

(2) Examples of Other Substances

1) Enzymes such as prostatic acidic phosphatase (PAP), prostate-specific angigen (PSA), alkaline phosphatase, transaminase, lactic acid dehydrogenase (LDH), transaminase, trypsin and pepsinogen.
2) Cancer-specific substances such as α-fetoprotein (AFP) and cancer embryonal antigen (CEA).
3) Serum protein components such as immunoglobulin G (IgG), fibrin-fibrinogen decomposition products (FDP, D-dimer), antithrombin III (ATIII) and transferrin.
4) Substances such as rheumatoid factor, serotonin, urokinase, ferritin and substance P.

Many substances such as other in vivo components and metabolites thereof are also included.

Examples of Hapten (Incomplete Antigen)

(1) Steroidal Haptens

1) Estrogens such as estrone, estradiol, estriol, estetrol, equilin and equilenin.
2) Natural or synthetic luteohormones such as progesterone, pregnanediol, pregnanetriol, 19-norethisterone and chloromadinone acetate.
3) Male sex hormones such as testosterone, dehydroepiandrosterone, dihydrotestosterone, androsterone and etiocholanorone.
4) Adrenal cortical hormones such as cortisol, cortisone, deoxycorticosterone, aldosterone and tetrahydrocortisol.
5) Bile acids such as vitamins D, cholesterol, cholic acid, deoxycholic acid and chenocholic acid, and other steroids such as cardiotonic steroid, saponin and sapogenin.

(2) Physiologically Active Amines

1) Catecholamines such as epinephrine, norepinephrine, dopamine and ephedrine, and metabolites thereof.
2) Physiologically active alkaloids such as morphine, codeine, heroin, morphine chloride, cocaine, mescaline, papaverine, narcotine, yohimbine, reserpine, ergotamine and strychinine.
3) Amino group-containing psychotropics such as LSD, amphetamine, methanephetamine and meprobamate.

(3) Other Examples

1) Low-molecular-weight peptides having no antigenicity such as TRH and LH-RH.
2) Thyroid hormones such as diiodothyronine, triiodothyronine and thyroxine.
3) Prostaglandins such as prostaglandin E2, prostaglandin E3 and prostaglandin F1α.
4) Vitamins such as vitamin A, vitamins B (vitamins B1, B2, B6 and B12, and the like), vitamin E and vitamin K.
5) Antibiotics such as penicillin, actinomycin, chloromycetin and tetracycline.
6) Other in vivo components, and drugs administered into organisms and metabolites thereof.

The sample (specimen) that can be used in the present invention maybe selected from any samples containing the above analytes, while it mainly includes in vivo substances such as urine, serum, plasma, blood, saliva and amniotic fluid.

The label that can work as an index for the presence or absence of an analyte may be any one of direct labels and indirect labels. A direct label is preferred in that the assay result can be visually observed so that no additional treatment or step is required. An indirect label requires treatment, a step or an apparatus for visualizing the label after the assay is completed.

The label substance that can be used as a direct label includes colored substances such as metal sol, colored latex particles, a color indicator, colored substances contained in liposome, various dyes and various pigments, and the like; non-metal sols such as carbon sol; chemiluminescence substances such as luminol derivatives and acridinium ester; and fluorescence substances such as fluorescein and rhodamine, while the label substance shall not be limited to these.

The label substance that can be used as an indirect label includes various enzymes such as peroxidase, β-galactosidase, alkaline phosphatase, urease and glucoseoxidase, while it shall not be limited to these.

When the direct label is used, the detection is carried out by the visual observation of a color tone or the measurement of a color density, luminescence intensity or fluorescence intensity. When the indirect label is used, the detection is carried out by the measurement of a color density or a luminescence intensity obtained by a change in an enzyme substrate or chromogen caused by an enzyme used.

Each of the semi-quantitative assay method and the semi-quantitative assay apparatus of the present invention will be explained hereinafter.

The semi-quantitative assay method of the present invention has characteristic features in that, for assaying an analyte in a sample, a certain amount of the analyte in the sample is trapped with a trapping antibody which is present being fixed in a predetermined amount, the certain amount depending upon the fixed amount (concentration) of the trapping antibody, so that the concentration of the analyte to be subjected to (having something to do with) the subsequent immunochemical qualitative analysis is decreased, whereby the same effect (dilution effect) as that obtained by using an analyte having a concentration diluted in advance is obtained, and the semi-quantitative assay can be carried out accurately without diluting the sample.

The analyte is classified into a complete antigen and a hapten, and the semi-quantitative assay method of the present invention will be explained more in detail on each case hereinafter.

I. A case where the analyte is a complete antigen.

Figure 2:
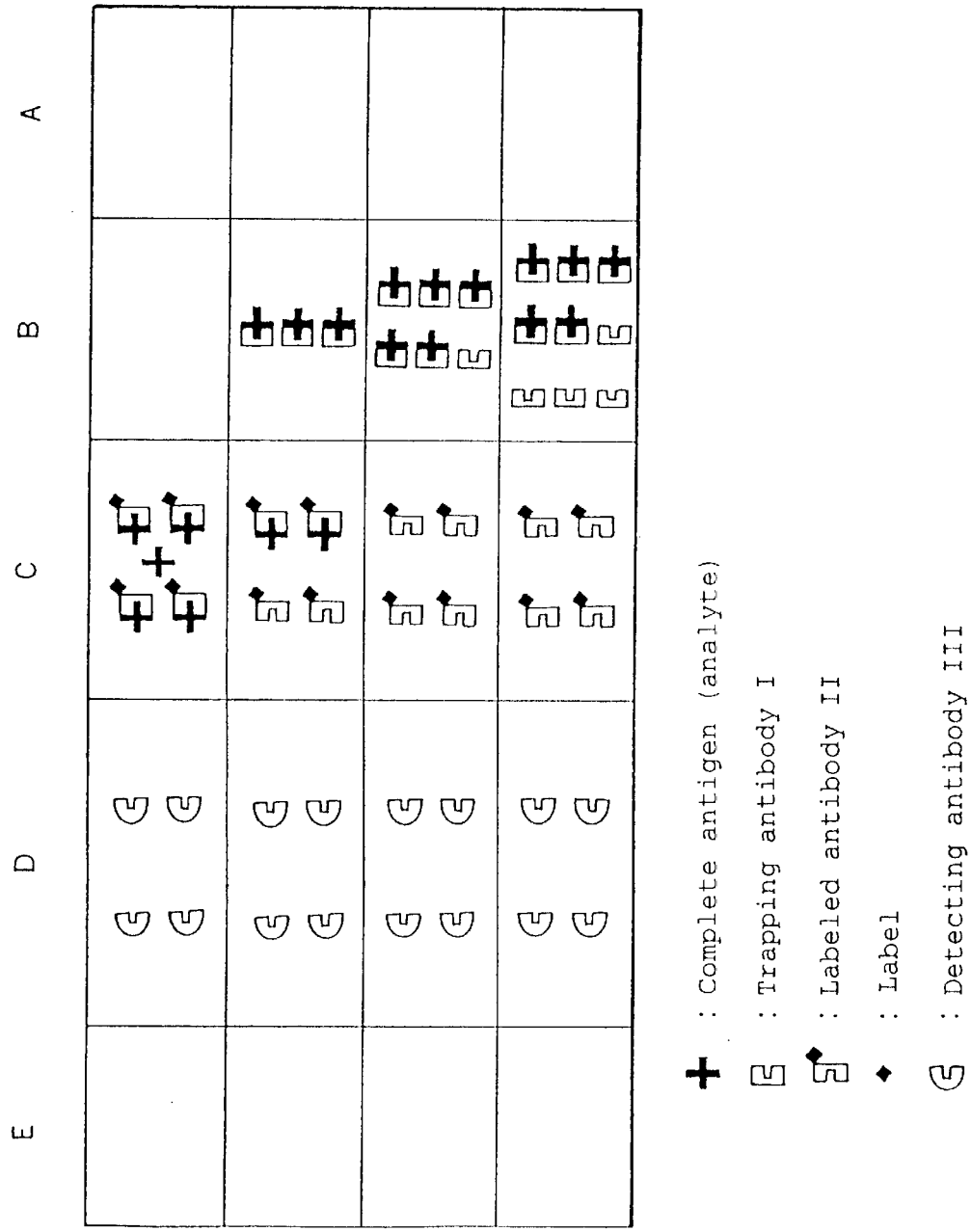
FIG. 2 shows the principle of the semi-quantitative assay method of the present invention when the analyte is a complete antigen (at the time when an assay is proceeding).
Figure 3:
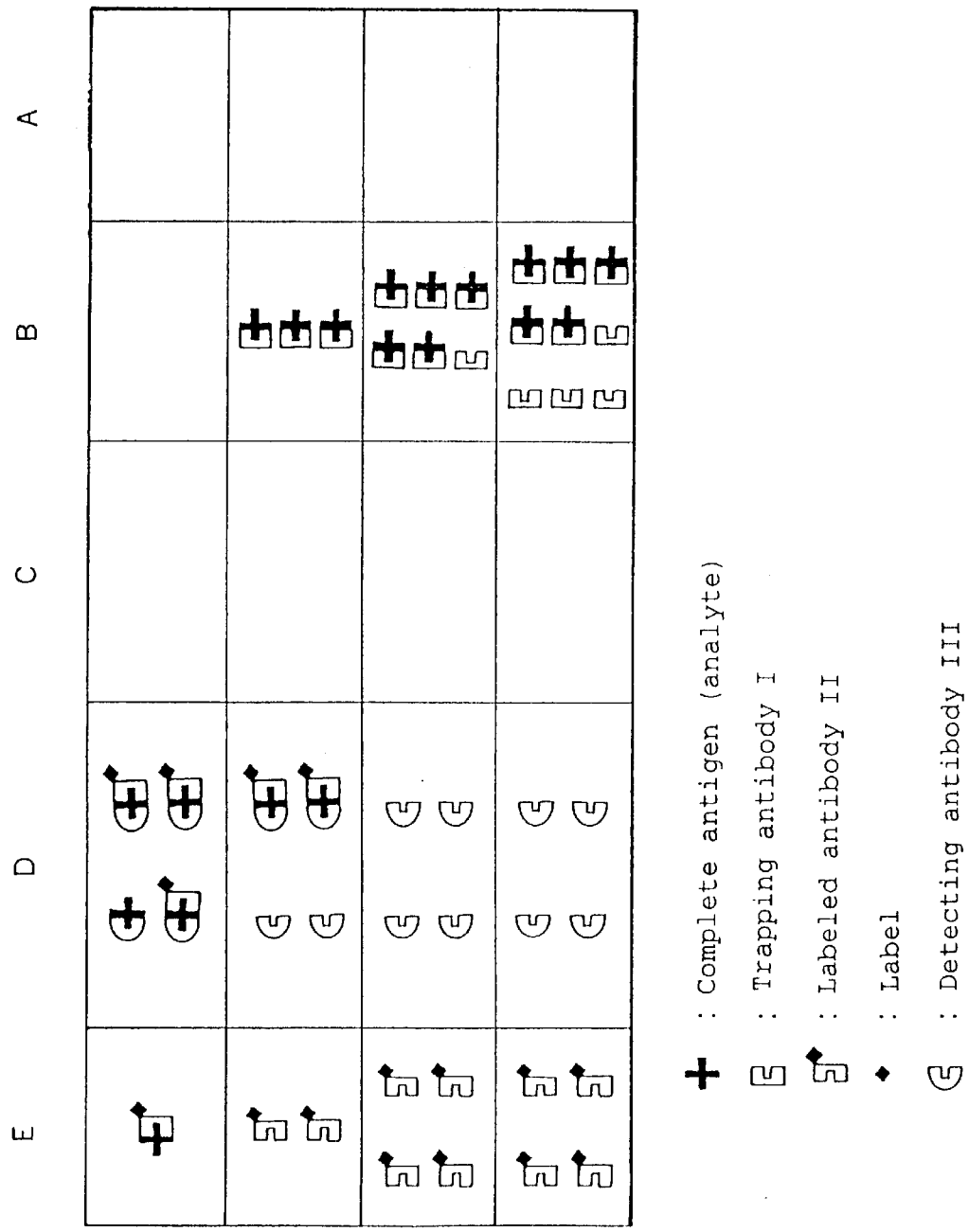
FIG. 3 shows the principle of the semi-quantitative assay method of the present invention when the analyte is a complete antigen (at the time when the assay has been completed).

The semi-quantitative assay method in this case is explained on the basis of FIGS. 1 to 3, which show an assay with the passage of time.

When the analyte in a sample is a complete antigen, in a reaction system constituted on the basis of the principle of an immunochemical sandwich reaction, the detecting substance is an antibody (to be referred to as "detecting antibody III", or simply as "antibody III", hereinafter), and the labeled substance is also a labeled antibody (to be referred to as "labeled antibody II", or simply as "antibody II", hereinafter). The antibody II and the antibody III are required to be antibodies which recognize different antigenic determinants on the same antigen (analyte).

The trapping antibody (to be referred to as "trapping antibody I, or simply as "antibody I", hereinafter) for trapping an analyte can be an antibody which recognizes the same antigenic determinant as that the antibody II or the antibody III recognizes, or which recognizes an antigenic determinant different from those which the antibody II and the antibody III recognize.

A sample having a certain concentration of an analyte is added to a sample addition portion (A) (FIG. 1), and chromatographically moved to an antibody-fixed portion (B) to allow the analyte to react with the trapping antibody I present being fixed thereto whereby a certain amount of the analyte depending upon the fixed amount of the antibody I is trapped. Then, the analyte which has not been trapped reacts with the labeled antibody II present in a labeled substance presence portion (C) in a state where the labeled antibody II is chromatographically mobile, to form an analyte-labeled antibody II complex (FIG. 2). And the complex chromatographically moves up to a detection portion (D) where the detecting antibody III is present being fixed, to form an antibody III-analyte-labeled antibody II sandwich complex, which is insolubilized and retained in the detection portion. The labeled antibody II which is not binding to any analyte and an excess of the analyte pass the detection portion (D), and moves to an absorption portion (E) to be removed out of the reaction system (FIG. 3).

The presence or the absence of the analyte is found by using, as an index, the label of the antibody III-analyte-labeled antibody II sandwich complex which is insolubilized and retained in the detection portion (D).

In the above method, the minimum detectable concentration (detection sensitivity) for the analyte is determined depending upon the amount of the detecting antibody III in the detection portion (D) and the amount of the labeled antibody II. When the analyte concentration in a sample is higher than the detection sensitivity, the sample is diluted by trapping the analyte in a certain amount depending upon the fixed amount of the antibody I in the antibody-fixed portion (B), whereby the same effect (dilution effect) as that obtained by decreasing the analyte concentration to a detection sensitivity can be obtained, and the semi-quantitative assay in a proper concentration width can be carried out by adjusting the amount of the antibody I in the antibody-fixed portion (B).

Each of the above antibody I and the antibody III may be any one of a polyclonal antibody and a monoclonal antibody, while a monoclonal antibody having high specificity is preferred in view of measurement sensitivity. The antibody II is required to be a monoclonal antibody which recognizes an antigenic determinant on the same antigen different from the antigenic determinant which the antibody I and the antibody III recognize, since the antibody II prevents the chromatographic movement if it reacts with an antigen to cause aggregation. The polyclonal antibody and the monoclonal antibody can be produced by known methods. For the polyclonal antibody, an animal is immunized with an antigen (analyte) to obtain an antiserum, and the intended antibody is separated from the antiserum, according to a conventional method. For the monoclonal antibody, for example, according to the general method by Kühler and Milstein (Nature 256 (1975) 495–497), mouse spleen cells immunized with an antigen (analyte) and myeroma cells are fused, fused cells which produce the intended antibody are selected, and the monoclonal antibody produced by the fused cells is obtained.

II. Case where the analyte is a hapten.

The semi-quantitative assay method is explained on the basis of FIGS. 4 to 6 and FIGS. 7 to 9 according to measurement principles.

When the analyte is a hapten, the principle is based on a competitive reaction to a detecting substance present being fixed in a detection portion (D).

Figure 4:
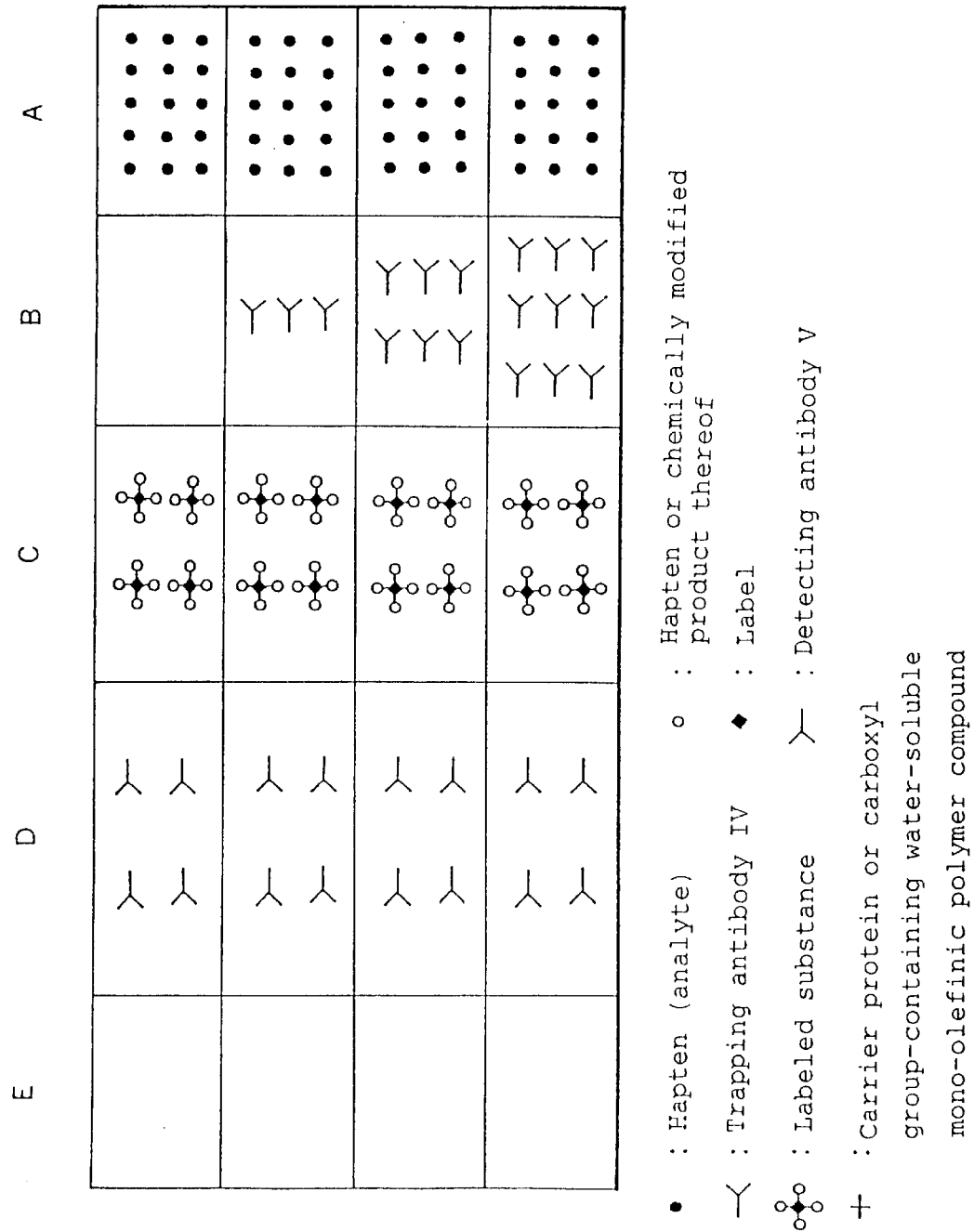
FIG. 4 shows the principle of the semi-quantitative assay method of the present invention when the analyte is a hapten (at the time when a sample is added).
Figure 5:
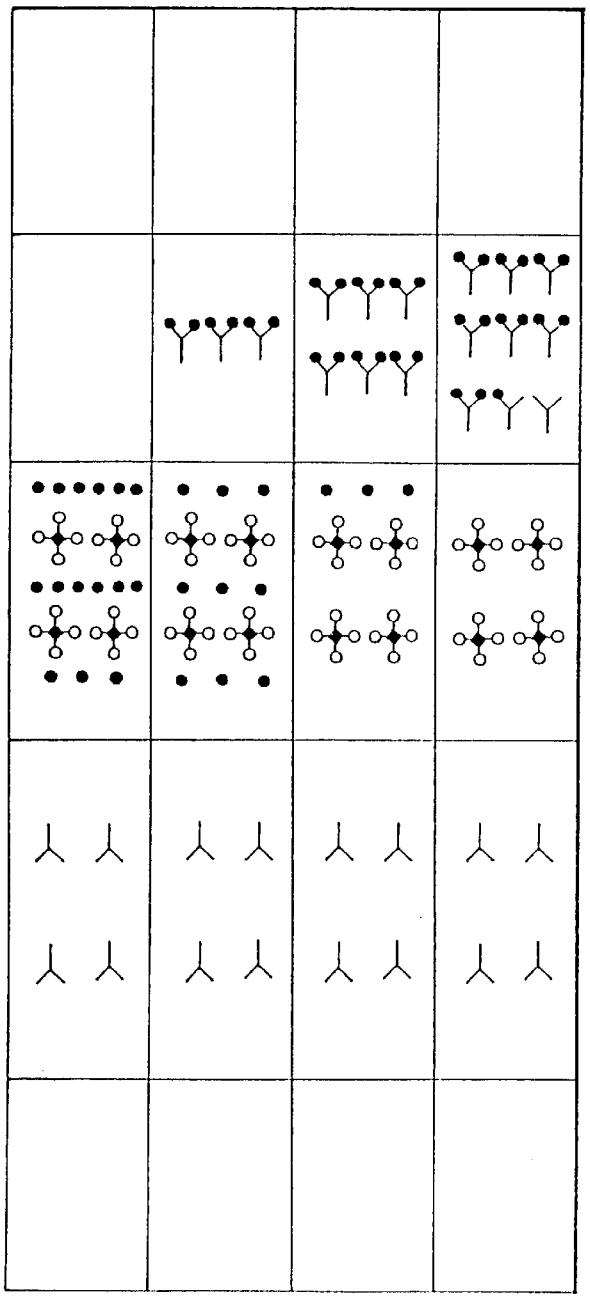
FIG. 5 shows the principle of the semi-quantitative assay method of the present invention when the analyte is a hapten (at the time when an assay is proceeding).
Figure 6:
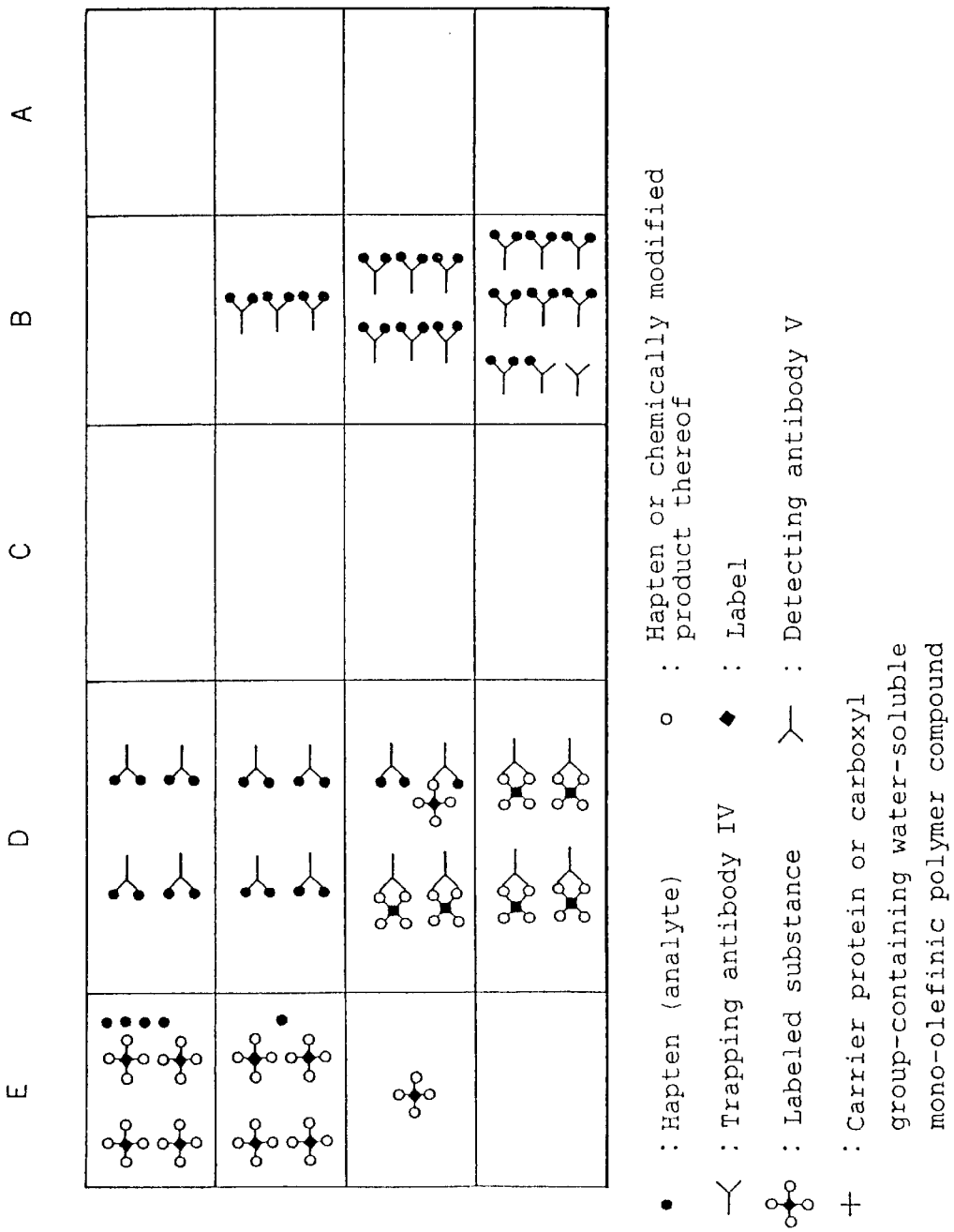
FIG. 6 shows the principle of the semi-quantitative assay method of the present invention when the analyte is a hapten (at the time when the assay has been completed).

(1) In the case of FIGS. 4 to 6, a hapten antibody (to be referred to as "detecting antibody V", or simply as "antibody VI", hereinafter) as a detecting substance is fixed in a detection portion (D), a labeled hapten-carrier protein combination or a labeled carboxyl group-containing water-soluble mono-olefinic polymer compound to which a hapten or a chemically modified product thereof is chemically bound (to be referred to as "label-hapten-carrier combination" hereinafter) as a labeled substance is held in a labeled substance presence portion (C) in a state that the label-hapten-carrier combination is chromatographically mobile, a hapten antibody (to be referred to as "trapping antibody IV", or simply as "antibody IV", hereinafter) is fixed in an antibody-fixed portion (B) as an antibody for trapping an analyte.

The hapten antibody IV and the antibody V are not required to be identical if they have the capability of binding to a hapten as an analyte. They may be those which bind to an analyte by a cross reaction to the hapten as an analyte.

The hapten as a component of the labeled substance may be a hapten which is the analyte, or may be a hapten which can bind to the antibody V by a cross reaction with a hapten as the analyte.

A sample having a certain concentration of an analyte is added to a sample addition portion (A) (FIG. 4) and moved to the antibody-fixed portion (B) by chromatographic movement to allow it to react with the trapping antibody IV. The analyte is trapped in a certain amount depending upon the fixed amount of the trapping antibody IV (FIG. 5). Then, the analyte which has not been trapped and the label-hapten-carrier combination which is present in the labeled substance presence portion (C) in a chromatographically mobile state move to the detection portion (D) by chromatographic movement, and competitively react with the detecting antibody V present being fixed to the detection portion (D). Those which have not bound in the detection portion chromatographically move to an absorption portion (E) and are removed out of the reaction system (FIG. 6).

In the above method, the minimum concentration (detection sensitivity) of the hapten as an analyte, which can competitively inhibit the binding reaction between the detecting antibody V and the labeled substance (label-hapten-carrier combination), is determined depending upon the amount of the detecting antibody V in the detection portion (D) and the amount of the labeled substance.

When the concentration of the analyte in a sample is higher than the detection sensitivity, the hapten as an analyte is trapped in a certain amount depending upon the fixed amount of the trapping antibody IV in the antibody-fixed portion (B) to decrease the concentration of the hapten as an analyte in the sample to the detection sensitivity, whereby the same effect (dilution effect) as that obtained by using a diluted sample can be obtained, and the semi-quantitative assay can be carried out in a proper concentration width by adjusting the fixed amount of the trapping antibody IV.

Figure 7:
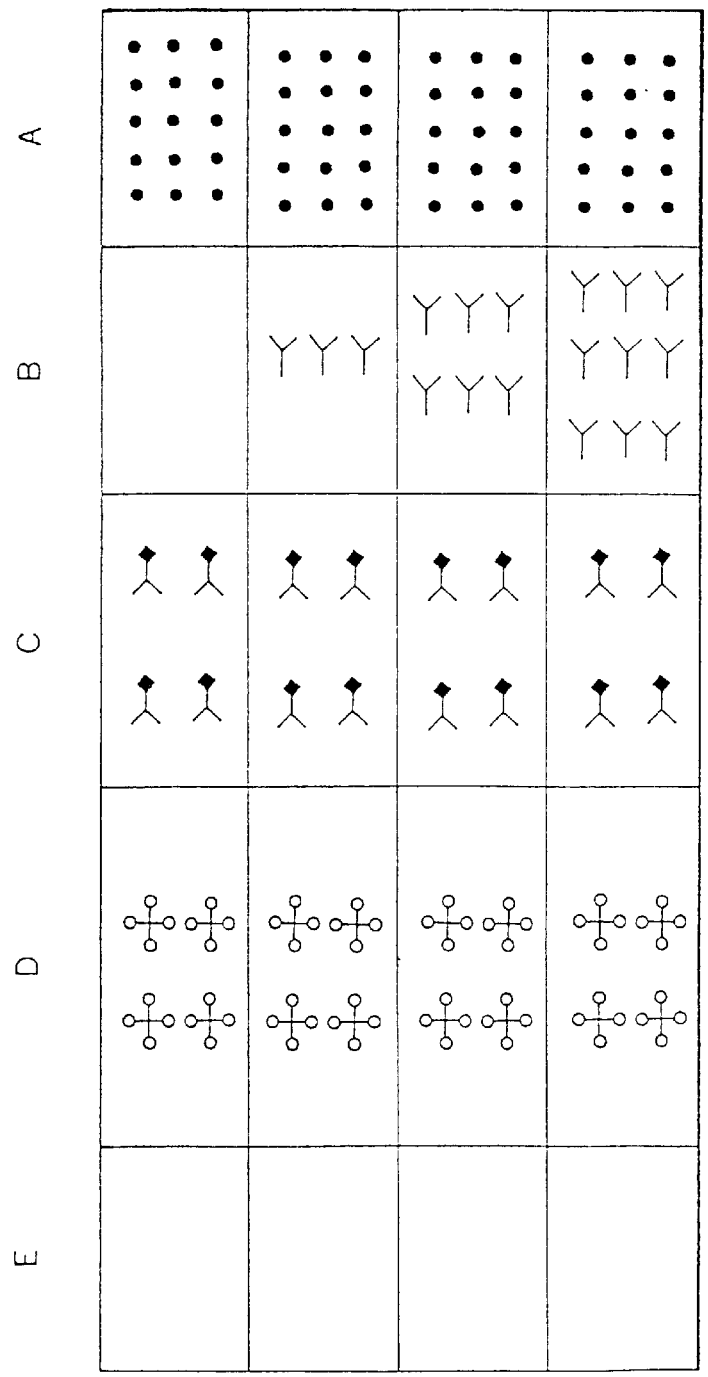
FIG. 7 shows the principle of the semi-quantitative assay method of the present invention when the analyte is a hapten (at the time when a sample is added).

(2) In the case of FIGS. 7 to 9, as a detecting substance, a hapten-carrier protein combination or a carboxyl group-containing water-soluble mono-olefinic polymer compound to which a hapten or a chemically modified product thereof is chemically bonded (to be referred to as "trapping hapten-carrier combination" hereinafter) is fixed in a detection portion (D). A labeled hapten antibody (to be referred to as "labeled antibody VII", or simply as "antibody VII", hereinafter) as a labeled substance is held in a labeled substance presence portion (C) in a state in which the antibody VII is chromatographically mobile. An antibody for trapping a hapten as an analyte (to be referred to as "trapping antibody VI", or simply as "antibody VI", hereinafter) is fixed in an antibody-fixed portion (B).

The trapping antibody VI in the antibody-fixed portion (B) and the labeled antibody VII in the labeled substance presence portion (C) are not required to be identical if they have the capability of binding to a hapten as an analyte. They may be those which bind to the hapten as an analyte by a cross reaction.

The hapten as a component of the detecting hapten-carrier combination insolubilized in the detection portion (D) may be a hapten as an analyte, or it may be a hapten which can bind to the labeled antibody VII by a cross reaction with the hapten as an analyte.

Figure 8:
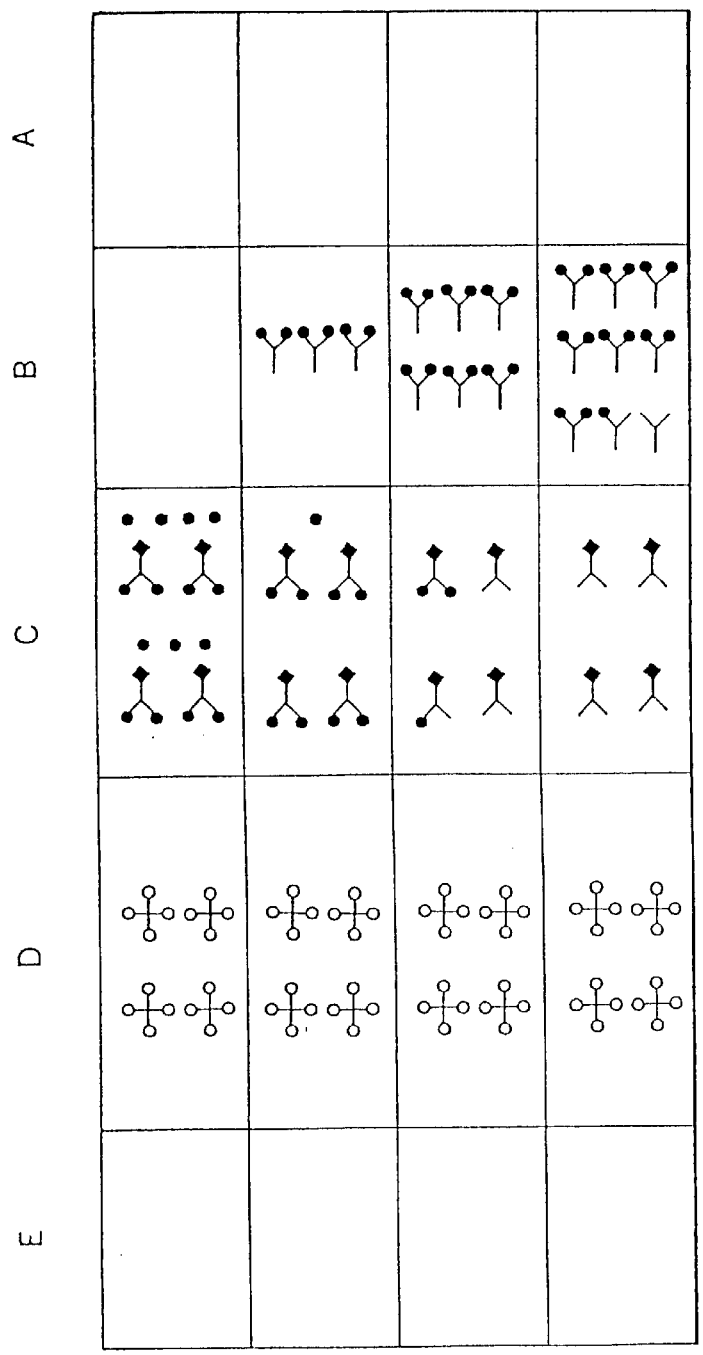
FIG. 8 shows the principle of the semi-quantitative assay method of the present invention when the analyte is a hapten (at the time when an assay is proceeding).

A sample containing a certain concentration of a hapten as an analyte is added to the sample addition portion (A) (FIG. 7), and it is moved to the antibody-fixed portion (B) by chromatographic movement and allowed to react with the trapping antibody VI to trap the hapten as an analyte in an amount depending upon the fixed amount of the trapping antibody The hapten as an analyte, which has not been trapped here, moves to the labeled substance presence portion (C) and reacts with the labeled antibody VII held in a chromatographically mobile state, to form an analyte hapten-labeled antibody VII complex (FIG. 8). The complex and unreacted labeled antibody VII moves to the detection portion (D), and the detecting hapten-carrier combination fixed therein and the unreacted labeled antibody VII bind to each other. Those which have not been bound in the detection portion (D) chromatographically move to an absorption portion (E) and are removed out of the reaction system (FIG. 9).

In the above method, the minimum concentration (detection sensitivity) of a hapten as an analyte, which can competitively inhibit the binding reaction between the detecting hapten-carrier combination present in the detection portion (D) and the labeled antibody VII in the labeled substance presence portion (C), is determined depending upon the hapten amount of the detecting hapten-carrier combination and the amount of the labeled antibody VII.

When the concentration of the analyte hapten in a sample is higher than the detection sensitivity, the hapten as an analyte is trapped in a certain amount depending upon the amount of the trapping antibody VI in the antibody-fixed portion (B) to decrease the analyte concentration in the sample, so that the same effect (dilution effect) as that obtained by diluting the sample to the detection sensitivity can be obtained, and the semi-quantitative assay in a proper width can be carried out by adjusting the amount of the trapping antibody VI in the antibody-fixed portion (B).

The above hapten antibodies used in the present invention may be conventional antibodies, or they may be monoclonal antibodies. These hapten antibodies can be produced by a conventional method. A hapten (analyte) or a chemically modified product thereof is coupled with a substance having antigenicity such as bovine serum albumin (BSA), and an animal is immunized therewith according to a conventional method, to obtain an antiserum. Then, an antibody having reactivity with a hapten (analyte) alone is separated from the so-obtained antiserum.

For a monoclonal antibody, spleen cells from a mouse immunized with the above antigen and myeroma cells are fused, fused cells which produce the intended antibody are selected, and the monoclonal antibody produced by the fused cells is obtained.

The hapten-carrier protein combination, or the hapten or its chemically modified product as a component of the carboxyl group-containing water-soluble mono-olefinic polymer compound to which the hapten or its chemically modified product is chemically bounded, participates in the competitive reaction. The carrier protein or the carboxyl group-containing water-soluble mono-olefinic polymer compound works for providing a site for binding to the labeled substance and a chromatographic material, and for improving the reactivity with the corresponding hapten antibody.

The carrier protein is selected from proteins derived from serum such as bovine serum albumin (BSA), rabbit serum albumin (RSA), goat serum albumin (GSA) and human serum albumin (HSA), and egg albumin (EA). When these are used, these proteins (e.g., BAS) are used for providing a hapten with antigenicity when the hapten antibody is produced, it is required to completely absorb and remove any antibody which can bind to these proteins.

The chemical modification of the hapten is carried out such that the hapten can chemically bond to the functional group (e.g., carboxyl group or hydroxyl group) of the carboxyl group-containing water-soluble mono-olefinic polymer compound (to be referred to as "spacer" hereinafter). The chemical modification can be carried by a known method, particularly preferably by a chemical modification method in which a carboxyl group, an amino group and a hydroxyl group are introduced into the hapten.

The spacer used in the present invention is a substance which is physiologically inactive and generally has no antigenicity. The spacer may have a hydroxyl group in addition to the carboxyl group, and these functional groups not only participate in the chemical bonding to the hapten or its chemically modified product, but also play a role in imparting the spacer as a polymer compound with solubility in water. The term "water solubility" of the spacer (carboxyl group-containing water-soluble mono-olefinic polymer compound) means that at least 1 part by weight of the spacer is completely dissolved in 1,000 parts of distilled water to form a transparent solution.

The average molecular weight of the spacer may be about 103~107 or more, and a spacer having an average molecular weight of approximately several tens of thousands to several millions is preferred.

Specific examples of the spacer include a homo- or copolymer of acrylic acid or methacrylic acid; a copolymer of maleic acid and vinyl acetate or a saponification product thereof, and a copolymer of maleic acid with vinyl alcohol, with lower alkyl vinyl ether, with acrylic acid or with lower alkyl ester thereof, or methacrylic acid or lower alkyl ester thereof, or a hydrolysis product thereof. Further, the spacer may be a copolymer of, e.g., acrylic acid or methacrylic acid and, e.g., β-hydroxylethyl ester of acrylic acid or acrylamide, or may be a terpolymer having constituent units from the above monomers.

The hapten or its chemically modified product and the spacer are chemically bonded in an amide bond or an ester bond, while an amide bond is preferred. The amide bond is formed, for example, by any one of known carbodiimide method, carbonyl diimidazole method, mixed acid anhydride method, active ester method, azide method, acid chloride method and diphenyl phosphoryl azide (DPPA) method. The carbodiimide method and the DPPA method are particularly preferred. Any one of the above methods may be used. Since, however, in some methods, a spacer is are unstable depending upon the presence of the functional group which belongs to the hapten but does not participate in the chemical bonding with the spacer, it is preferred to avoid any methods which require too severe conditions. The formation of the ester bond includes a case where the reactive hydroxyl group of the hapten or its chemically modified product and the carboxyl group of the spacer are bonded to each other, and a case where the functional groups are provided reversely. In the former case, the carboxyl group of the spacer is converted to a reactive derivative, e.g., acid chloride, and reacted with the hydroxyl group of the hapten, or when the spacer is a copolymer containing, e.g., maleic anhydride, it may be directed reacted with the hapten. In the latter case, the principle of the method for the formation of the ester bond is the same as that in the former case, while some haptens have no sufficient stability for converting its carboxyl group to a reactive derivative, e.g., acid chloride, and it is difficult in such a case to form the ester bond.

The semi-quantitative assay apparatus of the present invention will be explained on the basis of FIGS. 10, 11 and 12 hereinafter. FIGS. 10 and 11 show basic embodiments of the semi-quantitative assay apparatus of the present invention.

The semi-quantitative assay apparatus of the present invention is a chromatographic immunochemically analyzing apparatus having a sample addition portion (A), an antibody-fixed portion (B), a labeled substance presence portion (C), a detection portion (D) and an absorption portion (E) in this order.

In FIGS. 10 and 11, the labeled substance presence portion (C) may be positioned on the same chromatographic material (F) as that on which the detection portion (D) is positioned, and these portions may be formed of different materials. Further, the antibody-fixed portion (B) may be formed of a material different from that of the labeled substance presence portion (C) and/or the detection portion (D), and it may be positioned on the same chromatographic material (F) as that on which the labeled substance presence portion (C) and/or the detection portion (D) are/is provided.

Figure 10A:
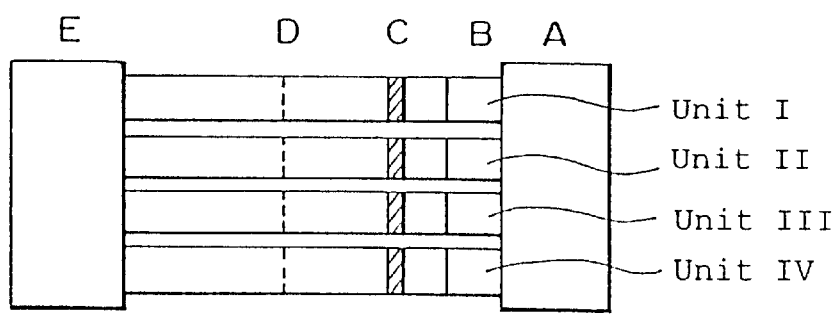
FIGS. 10A&B shows the basic constitution of the semi-quantitative assay apparatus of the present invention.

FIG. 10(a) shows a semi-quantitative assay apparatus which permits the semi-quantitative assay at four steps of concentration, and FIG. 11(a) shows a semi-quantitative assay apparatus which permits the semi-quantitative assay at six steps of concentration, while the number of steps of concentration can be decreased or increased as required. For example, the semi-quantitative assay apparatus in FIG. 10(a) is constituted of a sample addition portion (A) common to the four steps of concentration, four independent units, each unit being formed of three portions such as an antibody-fixed portion (B), a labeled substance presence portion (C) and a detection portion (D), and a common absorption portion (E). The amounts of the labeled substance in the labeled substance presence portion (C) and the amount of the detecting substance in the detection portion (D) in one unit are the same as those in another unit, while the fixed amount of the trapping antibody in the antibody-fixed portion (B) in one unit differs from that in another unit.

Figure 12E:
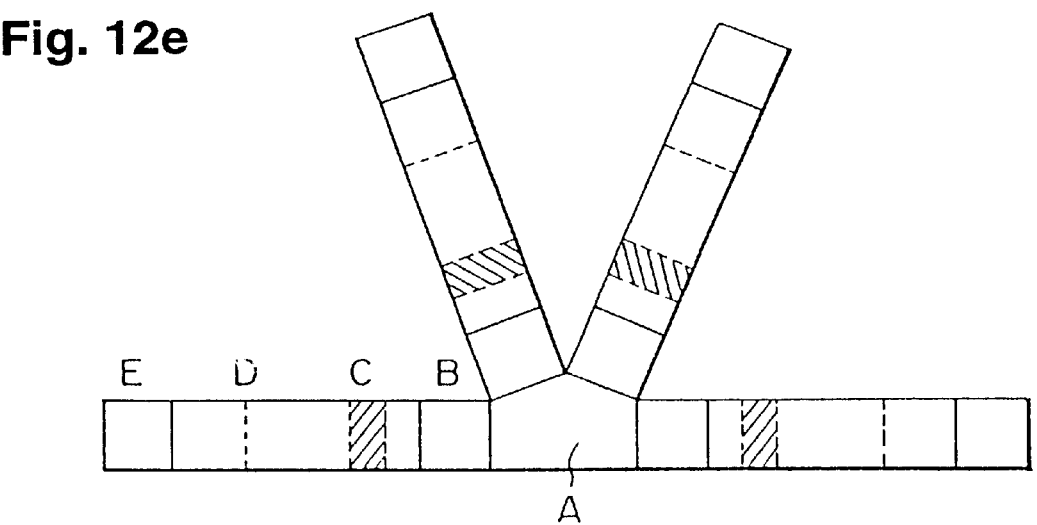
FIGS. 12E&F shows the constitution of the semi-quantitative assay apparatus of the present invention.
Figure 12F:
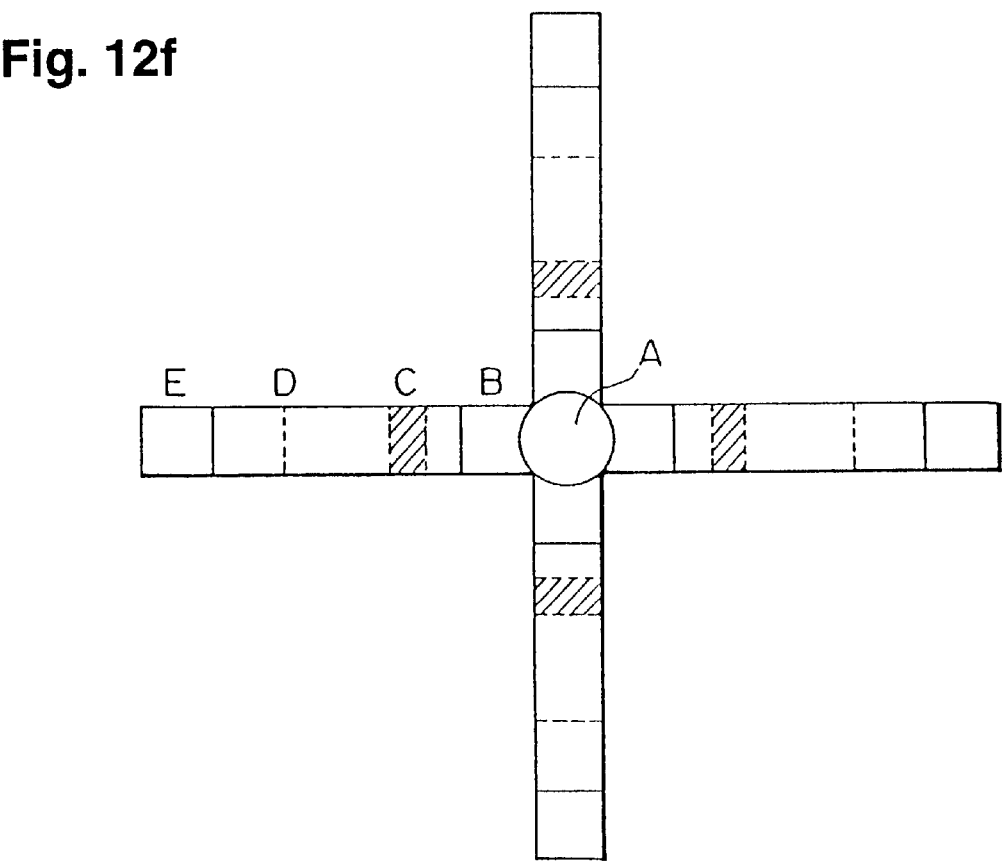

It is essential to form the sample addition portion (A) as one common portion for uniformly chromatographically providing each unit with a sample containing an analyte. For more uniform mobility of the sample to each unit, the constitution or arrangement shown in FIG. 12(e) and FIG. 12(f) is preferred. In these cases, the absorption portion (E) is provided to each unit.

Figure 11C:
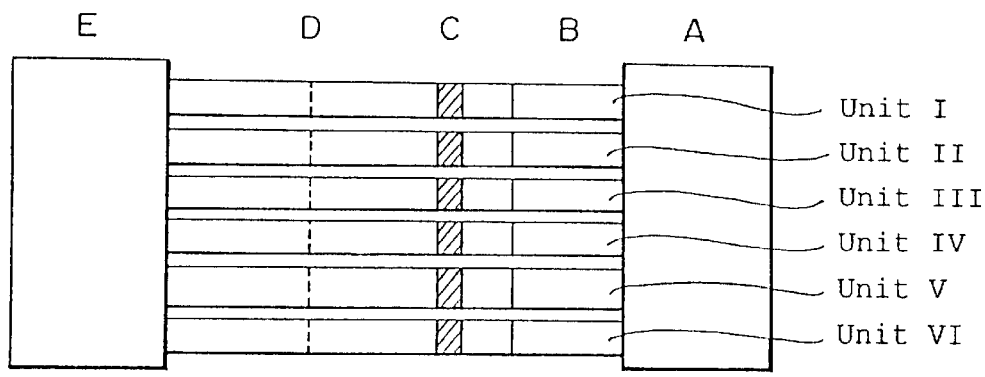
FIGS. 11C&D shows the basic constitution of the semi-quantitative assay apparatus of the present invention.
Figure 11D:
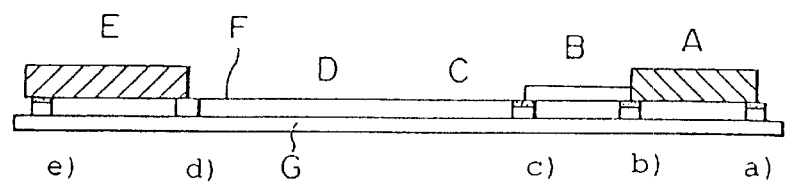

In the semi-quantitative assay apparatus of the present invention, materials for constituting the portions (A), (B), (C) and (D) are arranged on a support (G) such as a plastic plate, a glass plate or a film, preferably a plastic or glass plate to which an adhesive double-coated tape is applied, such that neighboring portions contact each other and that an added sample can be uniformly moved from (A) through (B), (C) and (D) by a capillary phenomenon, or as shown in FIG. 11(d), the above materials are arranged such that a chromatographic material including the detection portion (D) and the antibody-fixed portion (B) do not directly contact the support (G).

The constitution of each portion of the semi-quantitative assay apparatus of the present invention will be explained below.

Sample Addition Portion (A)

The material for the sample addition portion (A) includes those having homogeneous properties such as cellulose filter paper, glass fiber, polyurethane, polyacetate, cellulose acetate, nylon and cotton fabric, while the material shall not be limited to these.

The sample addition portion not only receives an added sample containing an analyte, but also has the function of filtering insoluble particles in the sample, so that a material which also has a filtering function such as cellulose filter paper or glass fiber filter paper is preferred.

For preventing the decrease in the semi-quantitative assay accuracy caused by the nonspecific adsorption of an analyte in a sample to the material forming the sample addition portion, it is preferred that the material for the sample addition portion should be treated in advance to prevent the nonspecific adsorption. The treatment to prevent the nonspecific adsorption is carried out, for example, by treatment with inactive protein or treatment with a surfactant. The treatment with inactive protein is carried out, for example, by immersing the material in a solution of 0.1~10% bovine serum albumin (BSA)-containing 0.1 M Tris buffer solution (pH 6~9), a solution of 0.1~10% skim milk powder 0.1 M Tris buffer solution (pH 6~9) and/or a 0.1~10% casein solution, allowing it to stand at 37° C. for 1 hour or at 4° C. for a whole day and night, washing it with a Tris buffer solution and drying it. The treatment with a surfactant is carried out, for example, by immersing the material in a solution containing 0.01 to 1% of Tween 20 or Triton X100 which is a nonionic surfactant, and drying it as it is. It is preferred to carry out both the treatment with inactive protein and the treatment with a surfactant before use of the material, although it depends upon kinds of the analyte and a sample.

Antibody-fixed Portion (B)

The material for the antibody-fixed portion preferably has homogeneous properties, can strictly define the fixed amount of the trapping antibody and is easily processable for size and thickness.

When it is intended to carry out the semi-quantitative assay using a large fixed amount (concentration) of the antibody for trapping an analyte, preferably, an activated filter paper sheet is used, and the trapping antibody is chemically bonded thereto. When the material is a CNBr activated cellulose, an activated cellulose filter paper sheet can be easily prepared by a known method such as the method of Ceska and Lundkvist (Immunochemistry, 9, 1021 (1972)), and the method of Lehtone, Viljanen et al (J. Immunol. Methods, 36, 63 (1980)) and ditto, 34, 61 (1980)).

When the material is DBM activated cellulose, it can be easily prepared by a known method such as the method of Alwine (Methods Enzymol., 68, 220 (1979)). Further, a commercially available activated nylon film (Pall Immunodyne) may be also used.

The chemical bonding of the trapping antibody to the above activated paper sheet can be also carried out according to a known method (LABORATORY TECHNIQUES IN BIOCHEMISTRY AND MOLECULAR BIOLOGY, Volume 15, Edited by R. H. BURDON and P. H. Van KNIPPENBERG ELSEVIER AMSTERDAM: NEW YORK, OXFORD (1985) P. 318–322). Further, the trapping antibody may be bound to the activated paper sheet through a second substance (antibody protein, etc.). When the second substance present therebetween is an antibody (to be referred to as "second antibody" hereinafter), and for example, when the trapping antibody to be fixed is a monoclonal antibody derived from a mouse, there may be used the activated paper sheet to which an excess of anti-mouse γG (gamma globulin) hetero-animal antibody is bound and then a proper amount of the trapping antibody is bound by an immunoreaction. When the substance present therebetween is a protein, for example, there may be used the activated paper sheet to which an excess of protein A is bonded and then a proper amount of the trapping antibody is bound.

When it is intended to carry out the semi-quantitative assay using a small fixed amount (concentration) of the antibody for trapping an analyte, the trapping antibody can be fixed upstream of the labeled substance presence portion (C) of a chromatographic material in the same manner as in the fixing of the detecting antibody (substance) in the detection portion (D).

Labeled Substance Presence Portion (C)

The labeled substance presence portion is produced by fixing the detecting substance in the detection portion (D) to be described later, carrying out the treatment of the chromatographic material to prevent the nonspecific adsorption to an analyte and the labeled substance and applying the labeled substance upstream of the detection portion of a chromatographic material, or by treating a cellulose filter paper sheet, glass fiber filter paper or unwoven fabric to prevent nonspecific adsorption, impregnating it with a certain amount of the labeled substance and drying it.

In the semi-quantitative assay method of the present invention, the solution velocity of the labeled substance and the uniformity of the chromatographic movement thereof influence the control of the measurement sensitivity in some cases, so that it is preferred to carry out the above treatment to prevent the nonspecific adsorption and the application of the labeled substance to a chromatographic material or the impregnation of the chromatographic material with the labeled substance in the presence of saccharides such as 0.1 to 10% mannitol or 0.1 to 30% saccharose.

Detection Portion (D)

The detection portion is produced by fixing the detecting substance in part of the chromatographic material.

The method of fixing the detecting substance includes a method in which the detecting substance is directly fixed to part of the chromatographic material by physical or chemical bonding, and an indirect fixing method in which the detecting substance is physically or chemically bonded to fine particles such as latex particles and part of the chromatographic material is allowed to trap the fine particles so that the fine particles are fixed. Any one of these methods may be used, while the direct fixing is preferred in the apparatus of the present invention in view of uniformity of insolubilization and easiness in sensitivity adjustment.

The material (chromatographic material) for constituting the detection portion is preferably selected from a porous nitrocellulose membrane, a porous cellulose film, a nylon film, a glass fiber, unwoven fabric, cloth and these materials which additionally have an active group to which the detecting substance is to bond. A porous nitrocellulose membrane and an activated nylon film are particularly preferred.

The form of the detecting substance fixed to the chromatographic material is not specially limited, and may be any form, while it is preferably a liner form across the chromatographic material so that the detection of the labeled substance is uniform with regard to the chromatographic movement leading end.

It is preferred to use the chromatographic material which has been treated with an inactive protein to prevent the nonspecific adsorption after the fixing of the detecting substance.

Absorption Portion (E)

The absorption portion is for physically absorbing added sample which has chromatographically moved and also for absorbing and removing unreacted labeled substance, etc., not insolubilized in the detection portion (D), and the absorption portion is formed from water-absorbing material such as cellulose filter paper, unwoven fabric, cloth or cellulose acetate.

The chromatographic movement rate after the chromatographic movement leading end of the added sample has reached the absorption portion differs depending upon the quality and size of the absorbing material, and the rate meeting the measurement of an analyte can be set depending upon the selection thereof.

The constitution of each portion of the semi-quantitative assay apparatus of the present invention is explained above, while the chromatographic movement rate (liquid flow rate) differs depending upon the factors such as the material, the size, the thickness, of each portion. These factors can be therefore selected and set as required such that the semi-quantitative assay can be most suitably carried out depending upon the kind of the analyte.

The measurement sensitivity of the present apparatus is mainly determined on the basis of the amount of the detecting substance fixed in the detection portion (D) and the amount of the labeled substance in the labeled substance presence portion (C). Further, the so-called dilution effect in the semi-quantitative assay of the present invention depends, in principle, on the fixed amount of the trapping antibody in the antibody-fixed portion (B), while the accuracy of the semi-quantitative assay depends upon the length and the thickness of the chromatographic material in the sample flow direction from the sample addition portion (A) to the detection portion (D), i.e., the passing liquid amount of the sample retaining the dilution effect. In particular, the amount of the sample liquid which gains the dilution effect in the antibody-fixed portion (B), out of the amount of a liquid which penetrates the antibody-fixed portion (B) from the sample addition portion (A), is to be sufficient for completely dissolving the labeled substance in the labeled substance presence portion (C) so that the dissolved labeled substance moves to the detection portion (D), which is the most important for carrying out the semi-quantitative assay of the present invention with good accuracy.

That is, the sample which has gained the dilution effect that the analyte has been trapped in a certain amount depending upon the fixed amount of the trapping antibody in the antibody-fixed portion (B), completely chromatographically moves the labeled substance up to the detection portion (D). As a result, even if another flow of the sample having the original concentration of the analyte reaches the detection portion (D) because the trapping antibody is saturated after the chromatographic movement is completed, the reaction in the detection portion (D) is not affected since the chromatographic movement of the labeled substance is completed, so that the assay result does not changed.

Therefore, the size of the antibody-fixed portion (B), i.e., the amount of sample liquid which passes the antibody-fixed portion (B) in a state where the sample has gained the dilution effect, is to be sufficient for completely chromatographically moving the labeled substance to the detection portion (D), which is essential for reliably materializing the dilution effect.

Further, as described concerning the constitution of the labeled substance presence portion (C), it is an important factor for improving the accuracy that the labeled substance is easily dissolved in the sample and moved.

EXAMPLES

The present invention will be more specifically explained with reference to Examples hereinafter.

Example 1

Measurement of hCG (Human Chorionic Gonadotropin)

1-a) Preparation of Anti-hCG Monoclonal Antibody

Balb/c mice were notally subcutaneously administered with both hCG (10,000 iu/mg) and Freund's complete adjuvant three times at intervals of 3 weeks, and further, after 3 weeks, the mice were intraperitoneally administered with hCG. Three days after the final immunization, spleen cells and myeloma cells (NS-1) were fused according to a conventional method, HAT selection was carried out, and cloning was repeated to give a fused cell strain to secrete an hCG-specific antibody and a fused cell strain to secrete a monoclonal antibody which recognized an a-subunit which cross-reacted with hCG, hLH and hFSH.

Each cell strain was intraperitoneally administered to Balb/c mice which were administered with Puristane in advance, to form ascitic tumor, and ascites was obtained. The so-obtained ascites was purified by ammonium sulfate fractionation and with an Affigel-protein A MAPS KIT, and freeze-dried to give a white powder of a monoclonal antibody.

The above-obtained anti-hCG-specific monoclonal antibody was used for producing an antibody-fixed portion (B) and a detection portion (D), and the monoclonal antibody which recognized an a-subunit was used for producing a labeled antibody.

1-b) Preparation of Colored Latex-labeled Anti-hCG-specific Antibody

The anti-hCG-specific monoclonal antibody obtained in 1-a), in an amount of 4 mg, was dissolved in 2 ml of glycine buffer solution (pH 8.2), and then while the solution was stirred, 1.0 ml of a red polystyrene latex (solid content 10%, supplied by Japan Synthetic Rubber Co., Ltd., particle diameter 0.303 µm) was dropwise added to, and mixed with, the solution. The mixture was continuously stirred at room temperature for 30 minutes and at 56° C. for 30 minutes. Then, the mixture was cooled and centrifugally separated. The resultant precipitate was suspended in 10 ml of a glycine buffer solution, and the centrifugal separation was repeated twice. Then, the precipitate was suspended in 10 ml of a 1% BSA-containing glycine buffer solution, and after the suspension was stirred at room temperature for 1 hour, the suspension was centrifugally separated. The operation of the centrifugal washing with a glycine buffer solution was repeated three times, and then, the precipitate was suspended in a glycine buffer solution containing 5% saccharose, 2.5% mannitol and 0.1% BSA, to produce an anti-hCG-specific monoclonal antibody-sensitized colored latex.

1-c) Preparation of Sample Addition Portion (A)

A sheet of filter paper for chromatography (supplied by Advantec Toyo, No. 585, thickness 0.85 mm) was cut to prepare 10×21 mm filter pieces, and these pieces were immersed in a 0.1 M Tris buffer solution (pH 8.2) containing 5% skim milk powder (Zenkoku Rakuno Rengokai; National Dairy Farming Association) and incubated at 37° C. for 1 hour. Then, the filter pieces were washed with a 0.1 M Tris buffer solution (pH 8.2) once, and then immersed in a 0.1 M Tris buffer solution (pH 8.2) containing 5% BSA Biocell Laboratories). The filter pieces were incubated at 37° C. for 1 hour, then washed with a 0.1 M Tris buffer solution (pH 8.2) once, drained, immersed in a 0.1 M Tris buffer solution containing 0.05% Tween 20, drained, and then dried at room temperature.

1-d) Preparation of Antibody-fixed Portion a) Preparation of CNBr Activated Cellulose Filter Paper A sheet of cellulose filter paper (supplied by Advantec Toyo, No. 50) was cut to 10×20 mm filter paper pieces, and 2 g of the filter paper pieces were immersed in 20 ml of purified water to swell them. Then, 60 ml of a CNBr solution (solution of 2.0 g of CNBr in 60 ml of purified water) was added, and immediately thereafter, the mixture was adjusted to pH 10.5 with 1N NaOH under stirring. Then, the mixture was maintained at pH of 10.5. with 1N NaOH for 30 minutes. After the reaction, the filter paper pieces were washed with 50 ml of $NaHCO_3$ twelve times, with 50 ml of purified water twice, with 50 ml of 20% acetone, with 50 ml of 50% acetone, with 70% acetone and with acetone twice each, and dried at room temperature. This CNBr activated cellulose filter paper was stored at 4° C. until used for the fixing of an antibody.

b) Preparation of Anti-hCG-specific Monoclonal Antibody-fixed Cellulose Filter Paper The anti-hCG-specific monoclonal antibody prepared in 1-a) and a coupling buffer solution (0.5M NaCl containing 0.1 M $NaHCO_3$, pH 8.3) were used to prepare solutions having anti-hCG-specific monoclonal antibody concentrations of 0, 0.1, 0.2 and 0.4 mg/ml. The CNBr activated cellulose filter paper prepared in the above a) was immersed in the solutions in an amount of 5 ml each with 10 sheets per solution, and the solutions were slowly stirred to carry out reactions at room temperature for 3 hours.

After the reaction, the filter paper pieces were washed with a coupling buffer solution twice and immersed in 1M ethanol amine solutions in an amount of 5 ml each with the 10 sheets per solution, and the solutions were slowly stirred at room temperature for 2 hours to block unreacted CNBr activated groups. Then, the filter paper sheets were washed with a 0.1M acetic acid buffer solution (pH 4.0)—a 0.1M Tris buffer solution (pH 8) three times, dried at room temperature and stored at 4° C. until they were used.

1-e) Preparation of Detection Portion (D)

A nitrocellulose membrane (supplied by Sartorius AG, pore diameter 8 μm) was cut to a size of 30×50 mm, 10 μl of a solution (50 μg/ml BSA-containing 50 mM Tris buffer solution (pH 8.2)) containing 1 mg/ml of the anti-hCG-specific monoclonal antibody prepared in the 1-a) was sprayed to the center (15 mm) of the cut nitrocellulose membrane with Cammg Linomat IV so that the sprayed solution had a linear form, and then, the cut nitrocellulose membrane was allowed to stand in a 25° C. constant-temperature and 80% constant-humidity chamber for 25 minutes. Thereafter, the resultant membrane was immersed in a solution of 5% skim milk powder (Zenkoku Rakuno Rengokai; National Dairy Firming Association) in a 0.1 M Tris buffer solution (pH 8.2) and in a 5% BAS solution for blocking, and then the membrane was washed with a 0.1 M Tris buffer solution containing 1% saccharose and 1% mannitol and dried by allowing it to stand at room temperature.

1-f) Preparation of Labeled Substance Presence Portion (C)

The colored latex-labeled anti-hCG antibody prepared in 1-b), in an amount of 20 μl, was sprayed to a position on the nitrocellulose membrane containing the detection portion (D), with a Cammg Linomat IV, the position being located 5 mm from one end of the membrane in parallel with the detection portion fixed in a linear form, and the membrane was dried at room temperature and stored at 4° C. until it was used.

1-g) Preparation of Apparatus

The nitrocellulose membrane containing the detection portion (D) and the labeled substance presence portion (C), prepared in 1-f), was cut through at right angles with the 50 mm width at intervals of 4 mm to prepare 4×30 mm strips. Further, 4×7 mm strips were also prepared from each of the anti-hCG-specific monoclonal antibody-fixed cellulose filter paper sheets produced by using antibody solutions in 1-d).

Figure 10B:
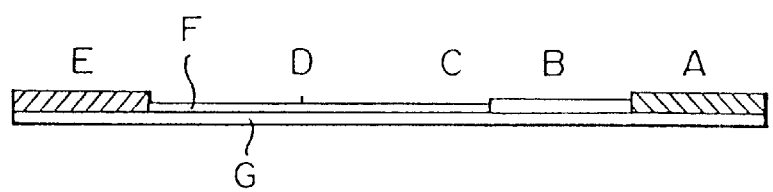

Four strips of the nitrocellulose membrane containing the detection portion (D) and the labeled substance presence portion (C) was attached to a support (G) prepared by attaching a coated adhesive tape on a glass plate as shown in FIG. 10(b), at intervals of 1 mm in parallel with one another as shown in FIG. 10(a). Thereafter, the strips of the anti-hCG-specific monoclonal antibody-fixed cellulose filter paper were attached such that 1 mm overlapped portions were formed on their right end, and further, the sample addition portion (A) prepared in 1-c) was attached such that a 1 mm overlapped portion was formed on its right end. On the other hand, a 10×21 mm filter paper piece from cellulose filter paper for chromatography (supplied by Advantec Toyo, No. 585) was attached to the left end of the membrane as an absorption portion (E) such that a 1 mm overlapped portion was formed, so that these were reliably connected. Five apparatus were produced in the same manner as above.

1-h) Measurement

Urine samples containing 0, 10, 20, 30 or 40 iu/l were used. One sample in an amount of 200 μl was added to one sample addition portion (A) of the apparatus prepared in 1-g), and another sample to another sample addition portion (A).

hCG in the samples was trapped in the antibody-fixed portion (B) in certain amounts based on the amounts of the trapping antibody, and then, remaining hCG was bound to the colored latex-labeled antibody, chromatographically moved, and bound to the anti-hCG-specific monoclonal antibody fixed in the detection portion (D) in a linear form. Unreacted labeled antibody and the sample solution were moved to the absorption portion (E) by chromatographic mobility, and thereafter, a coloring derived from the labeled substance in the detection portion (D) was observed.

The measurement sensitivity in the present apparatus was set at 10 iu/l on the basis of the amount of the anti-hCG monoclonal antibody fixed in the detection portion (D) and the amount of the colored latex-labeled antibody in the labeled substance presence portion (C), and the assay amount width was set on the basis of the amount of the trapping antibody in, and dimensions of, the antibody-fixed portion (B).

Colorings in the detection portions (D) of the apparatus to which the samples were added were as shown in Table 1(a). Table 1(b) shows a case in which a liner form in red was observed, as "+", and a case in which no linear form in red was observed, as "−".

TABLE 1

| | (Amount of trapping antibody) | (hCG concentration) | | | | |
|---|---|---|---|---|---|---|
| | | 0 | 10 | 20 | 30 | 40 iu/l |
| (a) | 0 mg/ml | | \| | \| | \| | \| |
| | 0.1 | | | \| | \| | \| |
| | 0.2 | | | | \| | \| |
| | 0.4 | | | | | \| |
| (b) | 0 mg/ml | − | + | + | + | + |
| | 0.1 | − | − | + | + | + |
| | 0.2 | − | − | − | + | + |
| | 0.4 | − | − | − | − | + |

As shown in Table 1, it has been found that the semi-quantitative assay of hCG in a sample can be carried out with good accuracy in a 10 iu/l concentration width according to the present invention.

Not being demonstrated in the above, for the semi-quantitative assay of a sample having an unknown concentration of hCG, preferably, the semi-quantitative assay is carried out by, first, setting the amounts of a fixed antibody at large widths, e.g., at four steps of 1,000, 200, 40 and 1 iu/l, and then, if the concentration of hCG in the sample is found to be in the range of 0 to 40 iu/l, repeating the same procedures as those described in the above Example 1. Further, when a sample has a concentration in other range, it is preferred to prepare and use a unit which permits the semi-quantitative assay depending upon the concentration.

Example 2

Measurement of hLH (Human Luteinizing Hormone)

2-a) Preparation of Anti-hLH Specific Monoclonal Antibody hLH was used as an antigen, and in the same manner as in Example 1-a), Balb/c mice were immunized, and cell fusion was carried out by using the spleen cells thereof, to give a fused cell strain to secrete an hLH specific monoclonal antibody and a fused cell strain to secrete a monoclonal antibody which recognized an a-subunit which cross-reacted with hCG, hLH and hFSH. Each cell strain was intraperitoneally administered to Balb/c mice which were administered with Puristane in advance, to form ascitic tumor, and ascites was obtained. The so-obtained ascites was purified by ammonium sulfate fractionation and with an Affigel-protein A MAPS KIT, and freeze-dried to give a white powder of a monoclonal antibody.

The above-obtained anti-hLH-specific monoclonal antibody was used for producing an antibody-fixed portion (B) and a detection portion (D), and the monoclonal antibody which recognized an a-subunit was used for producing a labeled antibody.

2-b) Preparation of Colloidal Gold-labeled Anti-hLH-specific Monoclonal Antibody The monoclonal antibody to recognize an hCG α-subunit, prepared in 2-a), was dissolved in 10 mM HEPES buffer solution (pH 7.4) to prepare a solution containing 200 μg/ml of the monoclonal antibody. The monoclonal antibody solution in an amount of 1.0 ml was added to 4.0 ml of a colloidal gold solution (colloidal gold particle diameter 10 nm, supplied by E-Y Laboratory), and the mixture was stirred at room temperature for 10 minutes. Then, 0.25 ml of 10 mM HEPES buffer solution (pH 7.4) containing 0.05% PEG20000 and 0.1% BSA was added, and the mixture was stirred for 1 hour and centrifugally separated at 15,000 rpm at 10° C. for 30 minutes. A 10 mM HEPES buffer solution (pH 7.4) containing 0.05% PEG20000, 0.1% BSA and 0.3 MD-mannitol, in an amount of 4.0 ml, was added to the resultant precipitate, and the precipitate was uniformly suspended in the 10 mM hepes buffer solution. Then, the mixture was further centrifugally separated at 10° C. at 15,000 rpm for 30 minutes, and 1.0 ml of the same buffer solution was added to the resultant precipitate, to give a colloidal gold-labeled anti-hLH antibody. The so-obtained antibody was stored at 4° C. until it was used.

2-c) Preparation of Sample Addition Portion (A)

A sheet of filter paper for chromatography (supplied by Advantec Toyo, No. 526) was cut to prepare 10×25 mm filter paper pieces, and a sample addition portion (A) was prepared therefrom in the same manner as in Example 1-c).

2-d) Preparation of Antibody-fixed Portion (B)

a) Preparation of CNBr Activated Cellulose Filter Paper

A sheet of cellulose filter paper (supplied by Advantec Toyo, No. 514A) was cut to 10×20 mm pieces, and CNBr activated cellulose filter paper was prepared from 2 g of the pieces in the same manner as in Example 1-d).

b) Preparation of Anti-hLH-specific Antibody-fixed Cellulose Filter Paper

The anti-hLH-specific monoclonal antibody prepared in 2-a) and a coupling buffer solution (0.5M NaCl containing 0.1 M NaHCO$_3$, pH 8.3) were used to prepare solutions having anti-hCG-specific monoclonal antibody concentrations of 0, 10, 25, 40, 70 and 120 μg/ml. The CNBr activated cellulose filter paper prepared in the above a) was immersed in the solutions in an amount of 5 ml each with 5 sheets per solution, and the solutions were slowly stirred for carrying out reactions at room temperature for about 3 hours and then at 4° C. overnight. After the reaction, unreacted active groups were blocked in the same manner as in Example 1-d), and the filter paper were washed with a 0.1M acetic acid buffer solution (pH 4.0)—0.1M Tris buffer solution (pH 8) three times, dried at room temperature and stored at 4° C. until they were used.

2-e) Preparation of Detection Portion (D)

A nitrocellulose membrane (supplied by Sartorius AG, pore diameter 8 μm) was cut to a size of 30×50 mm, 10 μl of a solution (50 μg/ml BSA-containing 50 mM Tris buffer solution (pH 8.2)) containing 200 μg/ml of the anti-hLH-specific monoclonal antibody prepared in the 2-a) was sprayed to the center (position located at 15 mm) of the cut nitrocellulose membrane with Cammg Linomat IV so that the sprayed solution had a linear form, and blocking and drying were carried out in the same manner as in Example 1-e), to give a nitrocellulose membrane containing a detection portion (D).

2-f) Preparation of Labeled Substance Presence Portion (C)

The colloidal gold-labeled anti-hLH-specific monoclonal antibody prepared in 2-b) was diluted twice with a 10% saccharose solution, and in the same manner as in Example 1-f), 50 μl thereof was sprayed to a position on the nitrocellulose membrane containing the detection portion (D) prepared in 2-e) in a linear form, with a Cammg Linomat IV, the position being located 7 mm from one end of the membrane in parallel with the detection portion, and the membrane was dried at room temperature and stored at 4° C. (in a desiccator) until it was used.

2-g) Preparation of Apparatus

The nitrocellulose membrane containing the detection portion (D) and the labeled substance presence portion (C), prepared in 2-f), was cut through at right angles with the 50 mm width at intervals of 3 mm to prepare 3×30 mm strips. Further, 3×10 mm strips were also prepared from each of the anti-hLH-specific monoclonal antibody-fixed cellulose filter paper sheets produced by using antibody solutions in 2-d).

An adhesive double-coated tape was attached to each top of projections a), b), c) and e) of a plastic plate provided with projections a) to e) shown in FIG. 11(d), and six strips of the nitrocellulose membrane containing the detection portion (D) and the labeled substance presence portion (C) was attached thereto with the adhesive tape on c) at intervals of 1 mm in parallel with one another as shown in FIG. 11(c). Thereafter, the strips of the anti-hLH-specific monoclonal antibody-fixed cellulose filter paper were attached such that 1 mm overlapped portions were formed on their right end, and further, the sample addition portion (A) prepared in 2-c) was attached such that a 1 mm overlapped portion was formed on its right end. On the other hand, a 10×25 mm filter paper piece from cellulose filter paper for chromatography (supplied by Advantec Toyo, No. 585) was attached to the left end of the membrane as an absorption portion (E) with the adhesive tape on e) such that a 2 mm overlapped portion was formed in a d) portion on a membrane (chromatographic material (F)).

Seven apparatus were produced in the above manner such that the membrane (chromatographic material (F)) and the antibody-fixed portion (B) did not directly contact the support.

2-h) Measurement

Urine samples containing 0, 50, 75, 100, 150, 200 and 300 miu/ml were used. One sample in an amount of 250 μl was added to one sample addition portion (A) of the apparatus prepared in 2-g), and another sample to another sample addition portion (A).

hLH in the samples was trapped in the antibody-fixed portions (B) in certain amounts based on the amounts of the trapping antibody, and then, remaining hCG was bound to the colloidal gold-labeled antibody, chromatographically moved, and bound to the specific monoclonal antibody fixed in the detection portion (D) in a linear form. Unreacted colloidal gold-labeled antibody and the sample solution were moved to the absorption portion (E) by chromatographic mobility, and thereafter, a coloring derived from the labeled substance in the detection portion (D) was observed.

The measurement sensitivity in the present apparatus was set at 50 miu/ml on the basis of the amount of the anti-hLH monoclonal antibody fixed in the detection portion (D) and the amount of the colloidal gold-labeled antibody in the labeled substance presence portion (C), and the semi-quantitative assay amount width was set on the basis of the amount of the trapping antibody in, and dimensions of, the antibody-fixed portion (B).

Colorings in the detection portions (D) of the apparatus to which the samples were added were as shown in Table 2(a). Table 2(b) shows a case in which a liner form in red was observed, as "+", and a case in which no linear form in red was observed, as "−".

TABLE 2

| (Amount of trapping antibody) | | (hLH concentration) | | | | | |
|---|---|---|---|---|---|---|---|
| | 0 | 50 | 75 | 100 | 150 | 200 | 300 miu/ml |
| (a) 0 μg/ml | | | | | | | |
| 10 | | | | | | | |
| 25 | | | | | | | |
| 40 | | | | | | | |
| 70 | | | | | | | |
| 120 | | | | | | | |
| (b) 0 μg/ml | − | + | + | + | + | + | + |
| 10 | − | − | + | + | + | + | + |
| 25 | − | − | − | + | + | + | + |
| 40 | − | − | − | − | + | + | + |
| 75 | − | − | − | − | − | + | + |
| 120 | − | − | − | − | − | − | + |

Example 3

Measurement of Estrogen 3-a) Preparation of Estriol-16-glucuronide-BSA

Estriol-16-glucuronide in an amount of 40 mg was dissolved in 1.0 ml of dimethylformamide (DMF), and 20.6 μl of tri-n-butylamine was added thereto at 4° C. or lower. Then, 11.2 μl of isobutyl chlorocarbonate was added, and the mixture was stirred for 30 minutes. This mixture was mixed with a liquid prepared in advance by dissolving 117 mg of BSA (bovine serum albumin) to 2.8 ml of water, adding 150 μl of a 1N NaOH solution, then adding 2.0 ml of dimethylformamide and keeping the mixture at 8° C. Then, the resultant mixture was stirred at 8° C., and after 1 hour, 16.6 μl of a 1N NaOH solution was added. The mixture was further stirred for 3.5 hours, and then unreacted estriol-16-glucuronide and reagents having a low molecular weight such as tri-n-butylamine, etc., were removed with Sephadex G-25. The resultant reaction mixture was dialyzed (with purified water), and then freeze-dried to give estriol-16-glucuronide-BSA. A Kobel reaction of the freeze-dry powder of the above antigen showed that 27 to 30 mol of estriol-16-glucuronide was bonded per mole of BSA.

3-b) Preparation of Anti-estriol-16-glucuronide Antibody

The estriol-16-glucuronide-BSA prepared in the above 3-a), in an amount of 2 mg, was dissolved in 1 ml of a saline solution, and emulsified with the same amount of Freund's complete adjuvant. The emulsion was injected into the foot pad and intradermic portion of a grown rabbit. This injection was carried out at intervals of 1 month, and after an increase in an antibody titer, whole blood was collected, and antiserum was obtained. The antiserum was inactivated at 56° C. for 30 minutes, absorbed with BSA, then salted out with ammonium sulfate, DEAE-cellulose chromatography and gel-filtered by Sephadex G200 to purify it, and then freeze-dried to give a white powder of anti-$E_3$16G antibody.

3-c) Preparation of Estriol-16-glucuronide-bonding Polyacrylic Acid ($E_3$16G-PAA)

a) Estriol-16-glucuronide-hexamethylenediamine Derivative

Estriol-16-glucuronide in an amount of 93 mg, and 25 mg of N-hydroxysuccinic acid imide were dissolved in 1.5 ml of DMF, and while the mixture was stirred with ice-cooling, 41 mg of dicyclohexylcarbodiimide(DCC) was added. After 30 minutes, a solution of 55 mg of monobenzyloxycarbonyl-hexamethylenediamine hydrochloride and 0.03 ml of triethylamine in 1 ml of DMF was added, and the mixture was stirred with ice-cooling for 2 hours and at room temperature for 12 hours. The reaction mixture as a whole was dried to solidness under reduced pressure, and the residue was subjected to preparative thin-layer chromatography to give 82 mg of the above-identified intended compound (yield relative to theoretical yield, 55%).

The above product showed an Rf=0.42 (chloroform-methanol 5:1) in silica gel thin-layer chromatography.

b) The estriol-16-glucuronide- hexamethylenediamine derivative obtained in the above a), in an amount of 50 mg, was dissolved in 3 ml of methanol, 10 mg of palladium black was added, and the mixture was stirred in hydrogen gas current at room temperature under atmospheric pressure. The reaction was completed in 2 hours, and the catalyst was removed by filtration. The filtrate was concentrated under reduced pressure, and a diethyl ether was added to the residue, to give 35 mg of a powder of the intended product in which carbobenzyloxy group was eliminated.

The above product in an amount of 10 mg was dissolved in 2 ml of DMF together with 100 mg of polyacrylic acid, 4 mg of DCC was added, and the mixture was allowed to stand at room temperature for 50 hours. The reaction liquid was dialyzed, and the dialyzed reaction liquid was filtered and freezed-dried to give 95 mg of estriol-16-glucuronide-bonded polyacrylic acid ($E_3$16G-PAA) in the form of a white powder.

3-d) Preparation of Colored Latex-labeled $E_3$16G-PAA

A 10% triethylamine solution prepared from N,N-dimethylformamide (DMF)purified water (1:1), in an amount of 12 ml, was added to, and suspended in, 0.5 ml of red aminated polystyrene latex (solid content 10%, supplied by Japan Synthetic Rubber Co., Ltd., particle diameter 0.37 µm), and the mixture was stirred for 15 minutes and then centrifugally separated. The precipitate was centrifugally washed with 10 ml of DMF water (1:1) twice and with 10 ml of purified water once, and then suspended in 0.5 ml of purified water, and the solution of $E_3 16G$-PAA prepared in 3a)(solution of 2 mg of $E_3 16G$-PAA in 1 ml of purified water) was added and mixed. Then, 7.5 mg of 1-ethyl-3-(3-dimethylaminopropyl)carbodiimide hydrochloride was added, and the mixture was allowed to react with stirring overnight. After the reaction, the reaction mixture was centrifugally separated, and the resultant precipitate was centrifugally washed with 10 ml of a glycine buffer solution three times and suspended in 10 ml of a glycine buffer solution containing 30% saccharose and 0.1% GSA (goat serum albumin) to obtain $E_3 16G$-PAA-bonded colored latex.

3-e) Preparation of sample addition portion (A)

A sheet of glass fiber filter paper (supplied by Advantec Toyo, GA-100, 2.1 φcm) was immersed in purified water to wash it, drained, and immersed in a 0.1 M Tris buffer solution (pH 8.2) containing 2% skim milk powder and 2.5% BSA. The sheet was allowed to stand at 4° C. for a whole day and night, then washed with a 0.1 M Tris buffer solution, drained and dried at room temperature.

3-f) Preparation of Antibody-fixed Portion (B)

a) Preparation of CNBr Activated Cellulose Filter Paper

A sheet of cellulose filter paper (supplied by Advantec Toyo, No. 526, thickness 0.70 mm) was cut to 10×20 mm pieces, and CNBr activated cellulose filter paper was prepared from 2 g of the pieces in the same manner as in Example 1-d).

b) Preparation of Anti-$E_3 16G$ Antibody-fixed Cellulose Filter Paper

The anti-$E_3 16G$ antibody prepared in 3-b) and a coupling buffer solution (0.5M NaCl containing 0.1 M NaHCO$_3$, pH 8.3) were used to prepare solutions having $E_3 16G$ antibody concentrations of 0, 0.25, 0.5 and 1.0 mg/ml. The CNBr activated cellulose filter paper prepared in the above a) was immersed in the solutions in an amount of 5 ml each with 5 sheets per solution, and the solutions were slowly stirred for carrying out reactions at room temperature for 2 hours. After the reaction, unreacted active groups were blocked in the same manner as in Example 1-d), and the filter paper sheets were washed with a 0.1M acetic acid buffer solution (pH 4.0)—0.1M Tris buffer solution (pH 8) three times, dried at room temperature and stored at 4° C. until they were used.

3-g) Preparation of Detection Portion (D)

A nitrocellulose membrane (supplied by Sartorius AG, pore diameter 5 µm) was cut to a size of 30 ×50 mm, 10 µl of a solution (50 µg/ml BSA-containing 50 mM Tris buffer solution (pH 8.2)) containing 0.25 mg/l of anti-$E_3 16G$ monoclonal antibody (supplied by Teikoku Hormone MFG, Co., Ltd.) was sprayed to a portion 10 mm apart from the membrane end with Cammg Linomat IV so that the sprayed solution had a linear form, the membrane was treated in the same manner as in Example 1-c), to give a nitrocellulose membrane containing a detection portion (D).

3-h) Preparation of Labeled Substance Presence Portion (C)

A polyester unwoven fabric (10×4 mm, thickness 0.5 mm) was immersed in a 0.1% solubilized case in solution, and allowed to stand at 37° C. for 1 hour. Then, the unwoven fabric was drained, impregnated with 20 µl of the colored latex-labeled $E_3 16G$-PAA suspension prepared in 3-d), dried at room temperature and stored in a desciccator until it was used.

3-i) Preparation of Apparatus

The nitrocellulose membrane containing the detection portion (D) prepared in 3-g) was cut through at right angles with the 50 mm width at intervals of 4 mm to prepare 4×30 mm strips. Further, 4×10 mm strips were also prepared from each of the anti-$E_3 16G$ antibody-fixed cellulose filter paper sheets produced by using antibody solutions in 3-f).

As shown in FIG. 12(f), an adhesive double-coated tape was attached to a glass plate (support (G)), the sample addition portion (A) prepared in 3-e) was attached to its center, and the strips of the anti-$E_3 16G$ antibody-fixed cellulose filter paper sheets prepared from the above solutions were attached around (A) at equal intervals such that 1 mm overlapped portions were formed (in the order of 0, 0.25, 0.5 and 1.0 mg/ml of antibody from one extending horizontally toward left hand side). The labeled substance presence portions (C) prepared in 3-h) were attached ahead thereof such that 2 mm overlapped portions were formed. Finally, 4×10 mm filter paper pieces from cellulose filter paper for chromatography (supplied by Advantec Toyo, No. 585) was attached as absorption portions (E) such that 2 mm overlapped portions were formed, so that these were reliably connected. Five apparatus were produced in the same manner as above.

3-j) Measurement

Urine samples containing 0, 1, 2, 4 and 8 µg/ml were used. One sample in an amount of 300 µl was added to one sample addition portion (A) of the apparatus prepared in 3-i), and another sample to another sample addition portion (A).

Estrogen in the samples was trapped in the antibody-fixed portions (B) in certain amounts based on the amounts of the trapping antibody, and then, the estrogen which was not trapped was chromatographically moved to the detection portions (D) together with the colored latex-labeled $E_3 16G$-PAA, and competitively bound to the anti-$E_3 16G$ antibody. Unreacted labeled substance was moved to the absorption portions (E) by chromatographic mobility, and thereafter, colorings derived from the labeled substance in the detection portion (D) were observed.

The detection sensitivity of the present apparatus was set such that 1 µg/ml of estrogen could inhibit a reaction between the antibody-$E_3 16G$ monoclonal antibody fixed in the detection portion (D) and the colored latex-labeled $E_3 16G$-PAA in the labeled substance presence portion (C) on the basis of the amount of the antibody-$E_3 16G$ monoclonal antibody and the amount of the colored latex-labeled $E_3 16G$-PAA, and the semi-quantitative assay width was set on the basis of the amount of the trapping antibody in, and the dimension of, the antibody-fixed portion (B).

Colorings in the detection portions (D) of the apparatus to which the samples were added were as shown in Table 3(a). Table 3(b) shows a case in which a liner form in red was observed, as "−", and a case in which no linear form in red was observed, as "+".

TABLE 3

| | (Amount of trapping antibody) | (Estrogen concentration) 0 | 1 | 2 | 4 | 8 μg/ml |
|---|---|---|---|---|---|---|
| (a) | 0 mg/ml | \| | | | | |
| | 0.25 | \| | \| | | | |
| | 0.5 | \| | \| | \| | | |
| | 1.0 | \| | \| | \| | \| | |
| (b) | 0 mg/mg | - | + | + | + | + |
| | 0.25 | - | - | + | + | + |
| | 0.5 | - | - | - | + | + |
| | 1.0 | - | - | - | - | + |

EFFECT OF THE INVENTION

The present invention provides a simple immunochemical semi-quantitative assay method which requires no dilution of a sample, which permits facile adjustment of "dilution effect" since the number of factors relating to the adjustment of the dilution effect is small, and which achieves excellent sensitivity, i.e., permits the setting of a narrow semi-quantitative assay value width, and an apparatus therefor.

What is claimed is:

1. An apparatus for an immunochemical semi-quantitative assay according to immunochromatography, the apparatus comprising a plurality of units, each unit comprising:

an antibody-fixed portion (B) where an antibody for trapping an amount of an analyte in a sample is present and fixed in a predetermined amount, a labeled substance presence portion (C) where a labeled substance as an index for detecting the presence of the analyte is present in a chromatographically mobile state, and a detection portion (D) where a detecting substance for detecting the labeled substance is present and fixed;

the apparatus comprising:

a plurality of said units arranged and spaced from each other, one sample addition portion (A) for adding the sample containing the analyte, the sample addition portion (A) provided for the plurality of said units, and an absorption portion (E) or absorption portions (E) for removing the labeled substance which does not participate in the detection of the analyte, together with the added sample, by absorption, the absorption portion (E) provided for the plurality of said units or the absorption portions (E) provided for the plurality of said units such that one unit has one absorption portion (E);

wherein the amount of the trapping antibody fixed in the antibody-fixed portion (B) of each unit differs from one unit to another and the amounts of the trapping antibodies are consecutively varied stepwise, the amount of the trapping antibody in one unit is zero, and the amount of the trapping antibody in at least one of the remaining units is an amount such that the analyte in the sample after trapping by the trapping antibody has a concentration below detection sensitivity, and wherein the analyte is a complete antigen, the labeled substance is a labeled antibody which recognizes an antigenic determinant on the analyte different from the trapping antibody, fixed to the antibody-fixed portion (B), and the detecting substance is a detecting antibody which recognizes an antigenic determinant on the analyte at least different from the labeled antibody.

2. The apparatus according to claim 1, wherein the analyte is human chorionic gonadotropin or human luteinizing hormone.

3. An apparatus for an immunochemical semi-quantitative assay according to immunochromatography, the apparatus comprising a plurality of units, each unit comprising:

an antibody-fixed portion (B) where an antibody for trapping an amount of an analyte in a sample is present and fixed in a predetermined amount, a labeled substance presence portion (C) where a labeled substance as an index for detecting the presence of the analyte is present in a chromatographically mobile state, and a detection portion (D) where a detecting substance for detecting the labeled substance is present and fixed;

the apparatus comprising:

a plurality of said units arranged and spaced from each other, one sample addition portion (A) for adding the sample containing the analyte, the sample addition portion (A) provided for the plurality of said units, and an absorption portion (E) or absorption portions (E) for removing the labeled substance which does not participate in the detection of the analyte, together with the added sample, by absorption, the absorption portion (E) provided for the plurality of said units or the absorption portions (E) provided for the plurality of said units such that one unit has one absorption portion (E);

wherein the amount of the trapping antibody fixed in the antibody-fixed portion (B) of each unit differs from one unit to another and the amounts of the trapping antibodies are consecutively varied stepwise, the amount of the trapping antibody in one unit is zero, and the amount of the trapping antibody in at least one of the remaining units is an amount such that the analyte in the sample after trapping by the trapping antibody has a concentration below detection sensitivity, and wherein the analyte is a hapten, the antibody for trapping the analyte, fixed in the antibody-fixed portion (B), is a hapten trapping antibody, the detecting substance is a hapten detecting antibody which binds to the analyte, and the labeled substance is a label-hapten-carrier combination which binds to the hapten detecting antibody competitively with the analyte.

4. The apparatus according to claim 1 or 3, wherein one absorption portion (E) is provided for a plurality of said units.

5. The apparatus according to claim 3, wherein the analyte is an estrogen.

* * * * *